(12) United States Patent
Woehr et al.

(10) Patent No.: US 6,623,458 B2
(45) Date of Patent: Sep. 23, 2003

(54) SPRING LAUNCHED NEEDLE SAFETY CLIP

(75) Inventors: Kevin Woehr, Felsberg (DE); Juergen Fuchs, Bad Emstal (DE); Helmut Freigang, Koerle (DE); Klaus Siemon, Koerle (DE)

(73) Assignee: B. Braun Melsungen, AG, Melsungen (DE)

( * ) Notice: Subject to any disclaimer, the term of this patent is extended or adjusted under 35 U.S.C. 154(b) by 0 days.

(21) Appl. No.: 09/965,055

(22) Filed: Sep. 26, 2001

(65) Prior Publication Data

US 2003/0060774 A1 Mar. 27, 2003

(51) Int. Cl.[7] ................................. A61M 5/32
(52) U.S. Cl. ...................... 604/192; 604/110; 604/198; 604/263; 128/919
(58) Field of Search ................... 604/162, 192, 604/263, 268, 110, 164.08, 198; 128/919

(56) References Cited

U.S. PATENT DOCUMENTS

| | | |
|---|---|---|
| 4,725,267 A | 2/1988 | Vaillancourt |
| 4,775,369 A | 10/1988 | Schwartz |
| 4,795,432 A | 1/1989 | Karczmer |
| 4,804,371 A * | 2/1989 | Vaillancourt ............... 604/198 |
| 4,813,940 A | 3/1989 | Parry |
| 4,846,809 A | 7/1989 | Sims |
| 4,850,977 A | 7/1989 | Bayless |
| 4,863,434 A | 9/1989 | Bayless |
| 4,863,435 A | 9/1989 | Sturman et al. |
| 4,887,998 A | 12/1989 | Martin et al. |
| 4,894,055 A | 1/1990 | Sudnak |
| 4,900,311 A | 2/1990 | Stern et al. |
| 4,927,416 A | 5/1990 | Tomkiel |
| 4,929,237 A | 5/1990 | Medway |
| 4,929,241 A | 5/1990 | Kulli |
| 4,955,866 A | 9/1990 | Corey |
| 4,978,344 A | 12/1990 | Dombrowski et al. |
| 4,985,021 A | 1/1991 | Straw et al. |
| 5,015,240 A | 5/1991 | Soproni et al. |
| 5,053,017 A | 10/1991 | Chamuel |
| 5,059,180 A | 10/1991 | McLees |
| 5,106,379 A | 4/1992 | Leap |
| 5,215,528 A | 6/1993 | Purdy et al. |
| 5,295,963 A | 3/1994 | Deeks |
| 5,322,517 A | 6/1994 | Sircom et al. |
| 5,328,482 A | 7/1994 | Sircom et al. |
| 5,334,158 A | 8/1994 | McLees |
| 5,344,408 A | 9/1994 | Partika |
| 5,364,370 A | 11/1994 | Szerlip et al. |
| 5,368,568 A | 11/1994 | Pitts et al. |
| 5,425,720 A | 6/1995 | Rogalsky et al. |
| 5,466,223 A | 11/1995 | Bressler et al. |
| 5,549,570 A | 8/1996 | Rogalsky |
| 5,554,131 A | 9/1996 | Lacivita |
| 5,584,818 A | 12/1996 | Morrison |
| 5,795,336 A | 8/1998 | Romano et al. |
| 5,817,070 A | 10/1998 | Tamaro |
| 5,879,337 A | 3/1999 | Kuracina et al. |
| 5,919,168 A | 7/1999 | Wheeler |
| 6,001,080 A | 12/1999 | Kuracina et al. |
| 6,171,284 B1 | 1/2001 | Kao et al. |

FOREIGN PATENT DOCUMENTS

NO    WP 02/00277 A2 *    6/2001

* cited by examiner

Primary Examiner—Brian L. Casler
Assistant Examiner—Lina R Kontos
(74) Attorney, Agent, or Firm—Christie, Parker & Hale, LLP

(57) ABSTRACT

A hypodermic needle assembly configured such that the movement of a needle shield into position to block the needle tip occurs as a direct consequence of a longitudinal force applied by insertion of a syringe plunger is provided. The hypodermic needle assembly according to the present invention comprises a needle, a needle hub, and a safety spring clip assembly, the safety spring clip assembly being configured to automatically launch from the needle hub and slide along the needle until the spring clip meets a needle stop at the needle tip, thus preventing the guard from being removed from the needle shaft. A method of using the hypodermic needle assembly according to the present invention is also provided.

46 Claims, 10 Drawing Sheets

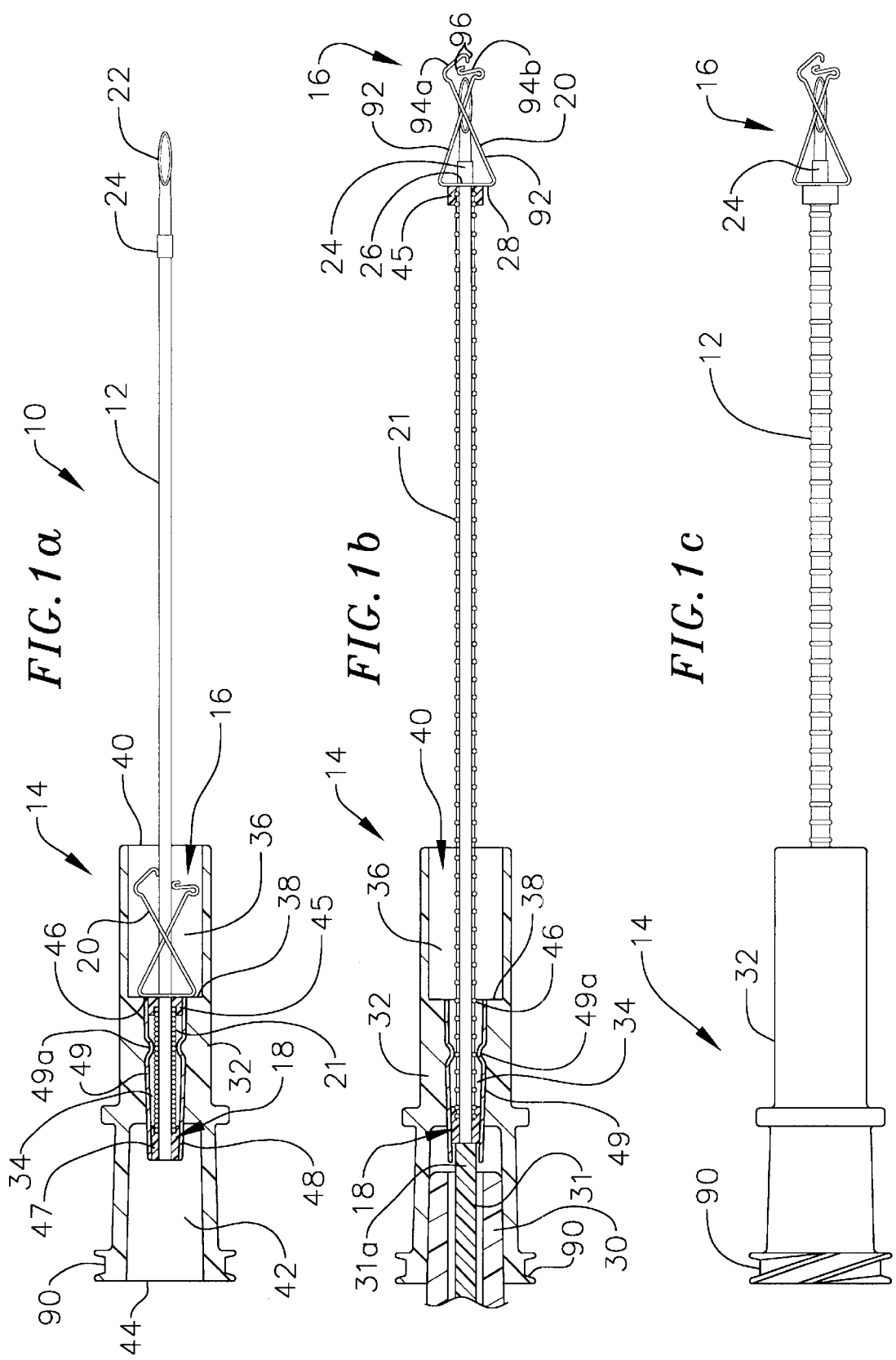

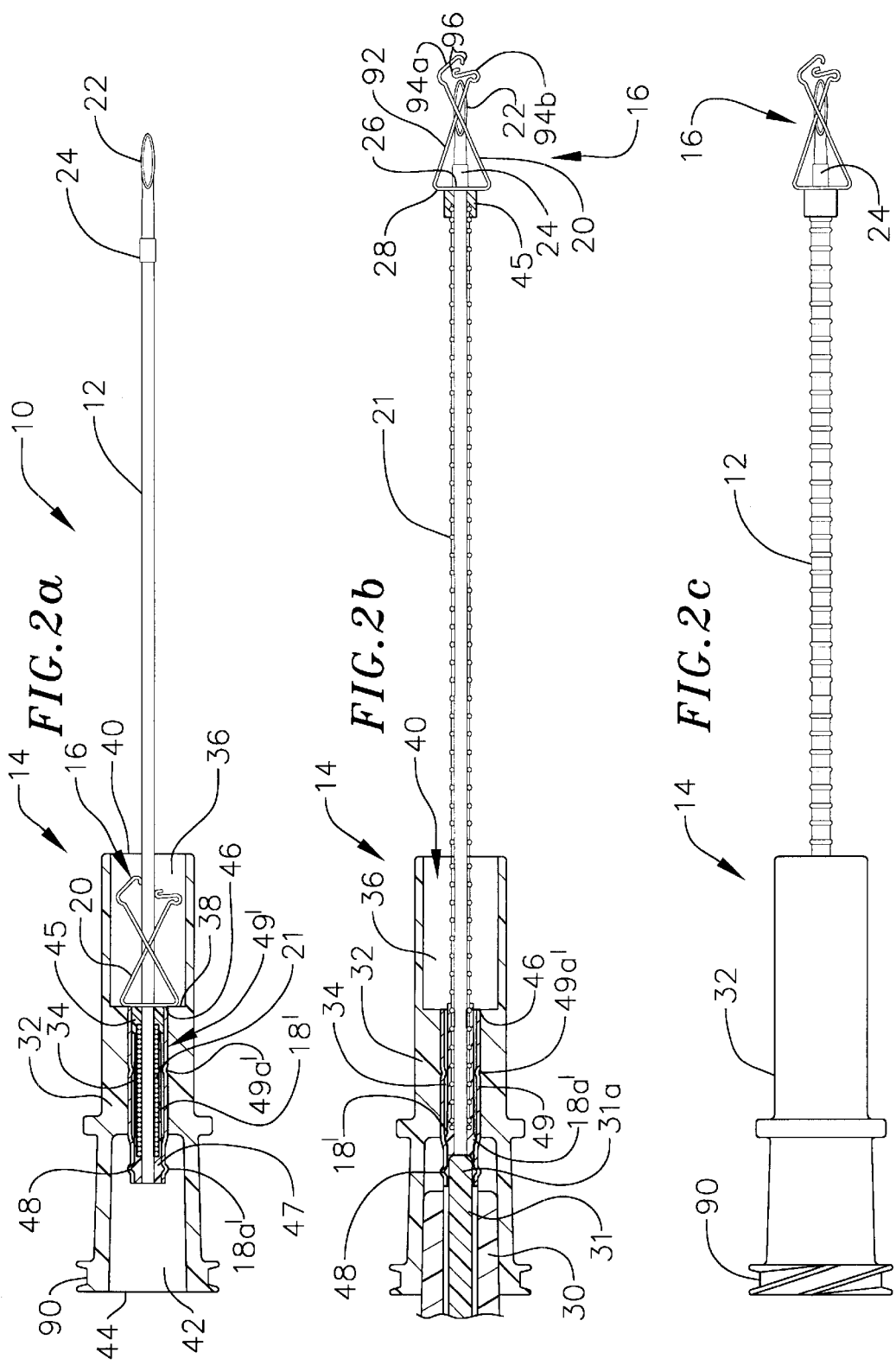

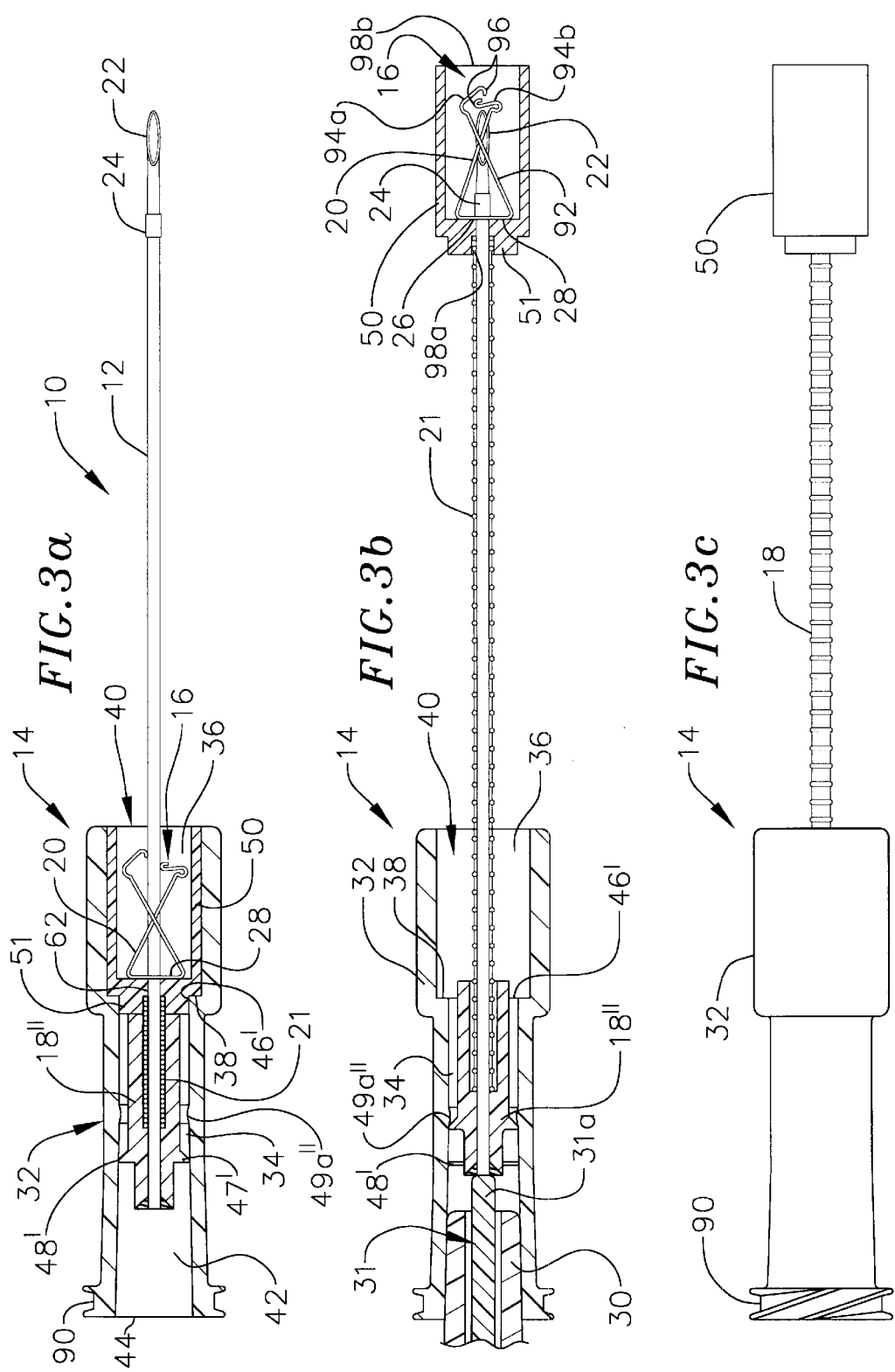

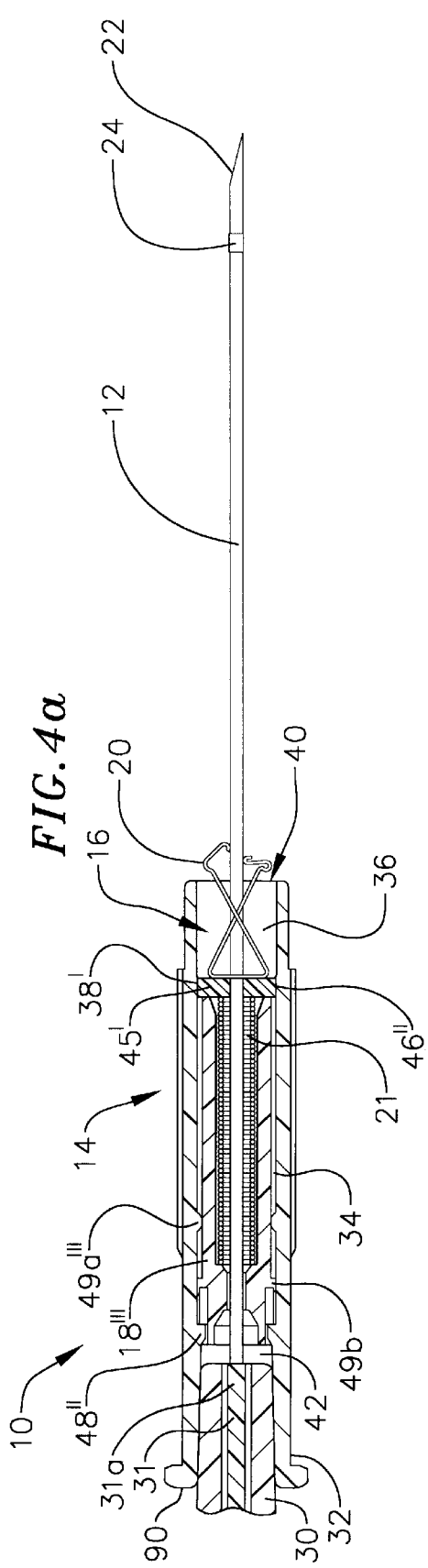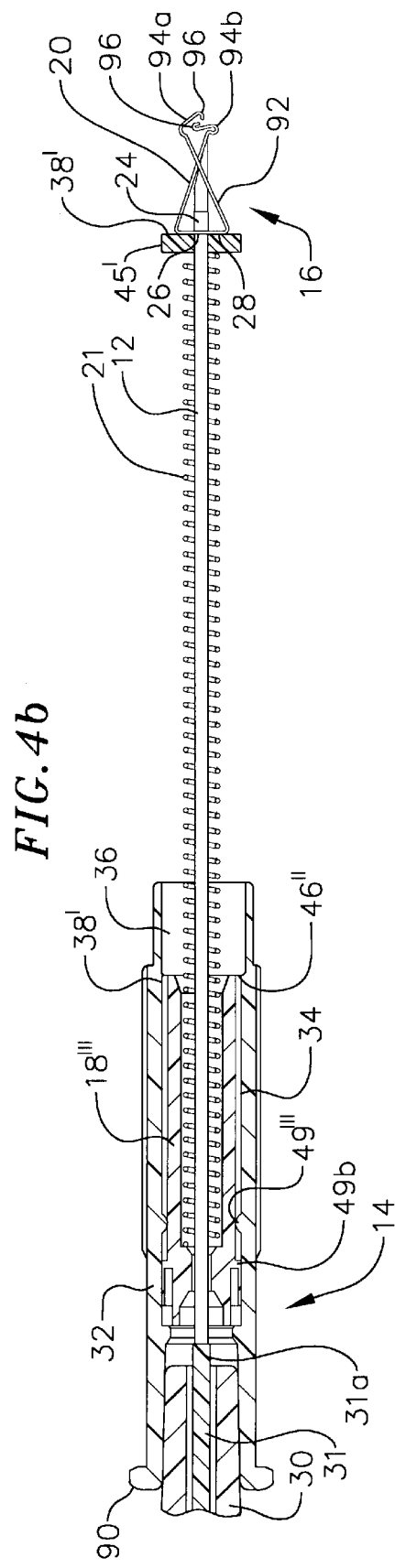

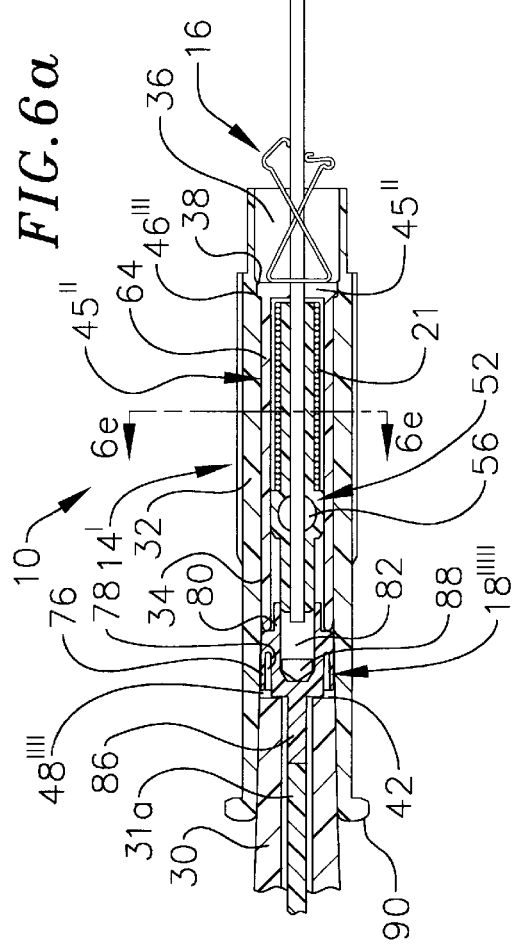
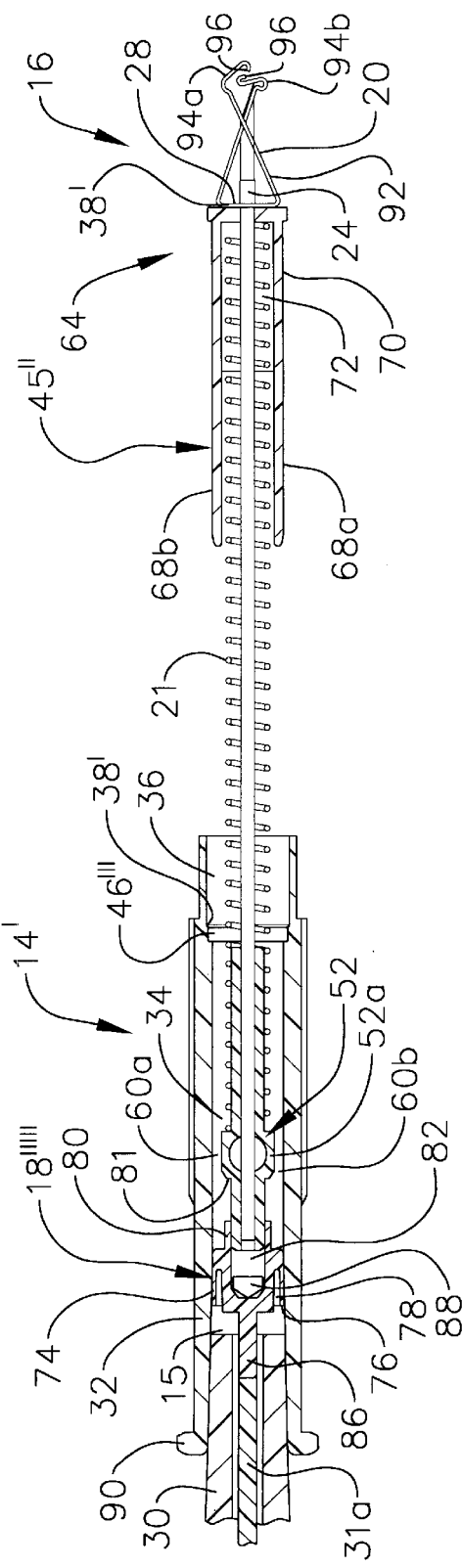

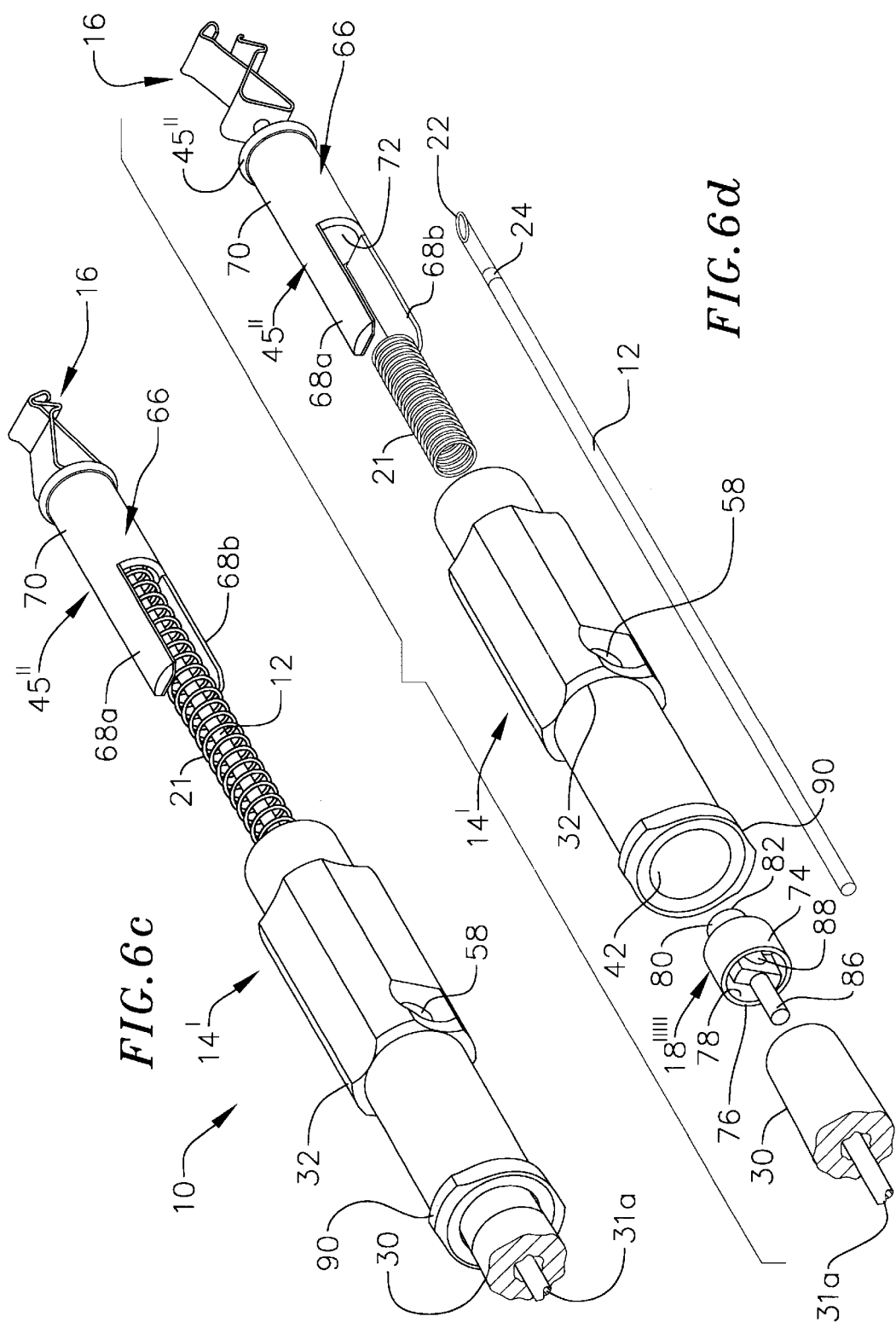

SPRING LAUNCHED NEEDLE SAFETY CLIP

FIELD OF THE INVENTION

This invention relates generally to hypodermic needle assemblies and more particularly to a hypodermic needle assembly having a resilient, member-launched safety clip device for blocking the tip of a disposable needle after use to facilitate the safe handling of hypodermic needles.

BACKGROUND OF THE INVENTION

Medical care of individuals requires the widespread use of needles for taking blood samples, intravenous drug delivery, and the introduction or removal of other fluids via cannula, needles, or syringes. In the current context, the use of hypodermic needles to deliver plasma, anesthetics, or other medications has become commonplace in medicine, science, veterinary medicine, and biotechnology. The use of a hypodermic needle typically involves first inserting a needle into the patient, injecting a substance or withdrawing a substance as required, and then removing the needle from the patient. In most applications, the withdrawn and contaminated needle must be handled very carefully during disposal to avoid needle stick injury.

To help prevent health care workers from becoming injured, guards have been developed to block the tip of these needles after use. Indeed, needle stick protection for medical professionals has become of particular importance in recent years because of the prevalence of potentially fatal infectious diseases, such as, for example, Acquired Immune Deficiency Syndrome (AIDS) and hepatitis, that can be transmitted by the exchange of bodily fluids through inadvertent wounds caused by accidental needle tip pricks after withdrawal from infected patients. Accordingly, many kinds of needle protection devices are available for providing post injection needle stick protection.

Devices which have been introduced to provide added protection against punctures by used needles fall into three basic categories, those which hide the withdrawn needle within a needle shield launched via a needle shield launching mechanism, those which require placement of a separate needle guard, and those which include a sliding shield which must be manually pushed along the needle shaft and over the tip of the used needle. Most of these needle guards are cumbersome and interfere with a single handed procedure, and or require additional complicated pieces to attach the needle guard to the needle tip.

Of the first type, i.e., devices which hide the withdrawn needle within a launched needle shield, there are several designs. However, all of these designs have undesirable features which make them unsuitable for many applications. For example, in one conventional design, a spring biased needle shield is provided which lockingly engages with the needle tip when the user manually activates the spring mechanism after the needle is withdrawn from the patient. However, while this mechanism provides for preventing the needle shield from disengaging and moving back down the length of the needle, the needle shields are only frictionally engaged to the tip of the needle, such that it is possible to slip the needle shield off of the distal end of the needle leaving the needle tip exposed. In addition, this design requires the user to manually activate the spring mechanism, which adds to the complexity of the design, manufacture, and use of the hypodermic needle assembly.

In another conventional design, the needle has a slightly expanded portion at the tip which prevents the needle shield from sliding off of the distal end of the needle once engaged. However, the needle shields utilizing this design still require the user to manually activate a second mechanism that then engages the needle guard, adding to the complexity of the design, manufacture and use of the hypodermic needle assembly.

Within this first category there are also a number of hypodermic needle assemblies for shielding the needle tip from being exposed once the needle is withdrawn from the patient which are automatically activated by the depression of the hypodermic plunger. However, the needle guards provided in most of these prior art designs consist of a simple hollow sleeve having an open distal end. While this design does provide protection from most inadvertent contact with the needle tip, it is still possible with such designs for a user to accidentally or purposefully insert a finger into the open distal end of the needle guard sleeve and thus come into contact with the contaminated needle tip.

Of the second and third types of needle shields, i.e., those which require placement of a separate needle guard or which use a shield that is manually pushed along a needle, there are several different designs. A number of these needle shields include either a spring-clip fitting or a frictional fitting, which are either placed directly on the tip of the needle or are movable from the base of the needle to the tip of the needle along the longitudinal direction of the needle. In the later embodiment, the user manually slides the needle shield toward the tip of the needle to thereby engage the needle shield around the needle tip. However, these manually activated designs require that the user either slide or apply the needle shield to the tip of the needle by hand, significantly raising the risk of unintentional contact with the needle tip.

Present day techniques thus offer a large number of solutions for protecting medical staff from used needles. However, as noted above, the known solutions suffer from at least one serious drawback. Accordingly, a hypodermic needle assembly is needed which reduces the risk of unintentional exposure of the used needle after use by automatically engaging the needle shield once injection is complete, without the need for additional complex mechanisms or cumbersome user operation.

SUMMARY OF THE INVENTION

According to the present invention, there is provided a hypodermic needle assembly designed such that the action of compressing the plunger of the syringe automatically activates a resilient, member-loaded needle shield such that the needle shield moves into position to block the needle tip, such that there is no risk of accidental injury and infection from an exposed needle and there is no need for the activation of any additional mechanisms to complete the needle shielding process.

The safety hypodermic needle assembly provided in accordance with practice of the present invention is a single-use device that is independent from the syringe assembly and is detachably attachable thereto. In one aspect, the safety hypodermic needle assembly comprises a needle hub having open proximal and distal ends, wherein the open proximal end defines a chamber configured to engage the tip of a syringe, and wherein the syringe tip has a plunger pin slidably mounted therein. A needle is provided which defines a longitudinal axis and has proximal and distal end portions. The distal end portion of the needle comprises a sharp needle tip, and the proximal end portion is mounted in the needle hub. The needle hub is configured such that the proximal end portion of the needle is in fluid communication with the syringe tip engagement chamber, and the distal end portion of the needle extends out from the distal end of the needle hub. A needle tip safety guard assembly is provided which comprises a needle tip safety guard which is mounted on the needle and arranged at the distal end portion of the needle hub. The needle tip safety guard assembly has a proximal end portion disposed within the open distal end of the needle hub, and the needle tip safety guard has a needle opening therein through which the needle extends. The needle tip safety guard assembly is configured such that when the needle tip safety guard is urged over the needle tip, the needle tip guard is engaged to block the needle tip. A needle guard activator assembly is provided for urging the needle tip safety guard in a distal direction along the needle. The activator assembly comprises a pressure trigger and a resilient member, wherein the pressure trigger is mounted in the needle hub and is arranged between the syringe plunger when the syringe tip is in the syringe tip engagement chamber and the needle tip safety guard, such that when the syringe plunger is translated distally, the plunger pin mechanically interacts with the pressure trigger. The pressure trigger is configured to transmit the force of the plunger pin longitudinally along the axis of the needle assembly in a distal direction, such that the resilient member is activated to urge the needle tip safety guard distally along the needle and over the needle tip to its blocking position. The needle tip safety guard is passively actuated so that the user is not required to perform any operations outside of those employed using conventional hypodermic needles. In order to use the safety hypodermic needle assembly, it is not necessary for the user to learn additional procedures. The needle tip safety guard automatically blocks the needle tip so that the user, or those who dispose of the used needle, are not subjected to inadvertent needle sticks.

BRIEF DESCRIPTION OF THE DRAWINGS

These and other features and advantages of the present invention will become appreciated as the same becomes better understood with reference to the specification, claims and drawings wherein:

FIG. 1a is a semi-schematic cross-sectional top view of an unactivated hypodermic needle assembly according to one embodiment of the present invention not yet attached to a syringe;

FIG. 1b is a semi-schematic cross-sectional top view of the hypodermic needle assembly of FIG. 1a shown in its activated state and attached to a syringe;

FIG. 1c is a semi-schematic top view of the hypodermic needle assembly of FIG. 1a shown in its activated state;

FIG. 2a is a semi-schematic cross-sectional top view of an unactivated hypodermic needle assembly according to a second embodiment of the present invention not yet attached to a syringe;

FIG. 2b is a semi-schematic cross-sectional top view of the hypodermic needle assembly of FIG. 2a shown in its activated state and attached to a syringe;

FIG. 2c is a semi-schematic top view of the hypodermic needle assembly of FIG. 2a shown in its activated state;

FIG. 3a is a semi-schematic cross-sectional top view of an unactivated hypodermic needle assembly according to a third embodiment of the present invention not yet attached to a syringe;

FIG. 3b is a semi-schematic cross-sectional top view of the hypodermic needle assembly of FIG. 3a shown in its activated state and attached to a syringe;

FIG. 3c is a semi-schematic top view of the hypodermic needle assembly of FIG. 3a shown in its activated state;

FIG. 4a is a semi-schematic cross-sectional top view of an unactivated hypodermic needle assembly according to a fourth embodiment of the present invention attached to a syringe;

FIG. 4b is a semi-schematic cross-sectional top view of the hypodermic needle assembly of FIG. 4a shown in its activated state and attached to a syringe;

FIG. 6a is a semi-schematic cross-sectional top view of an unactivated hypodermic needle assembly according to a seventh embodiment of the present invention attached to a syringe;

FIG. 6b is a semi-schematic cross-sectional top view of the hypodermic needle assembly of FIG. 6a shown in its activated state and attached to a syringe;

FIG. 6c is a semi-schematic perspective view of the hypodermic needle assembly of FIG. 6a shown in its activated state and attached to a syringe;

FIG. 6d is a semi-schematic exploded perspective view of the hypodermic needle assembly and syringe of FIG. 6a; and FIG. 6e is a semi-schematic cross sectional view of the hypodermic needle assembly taken along line 6e—6e of FIG. 6a.

DETAILED DESCRIPTION OF THE INVENTION

Figure 4C:
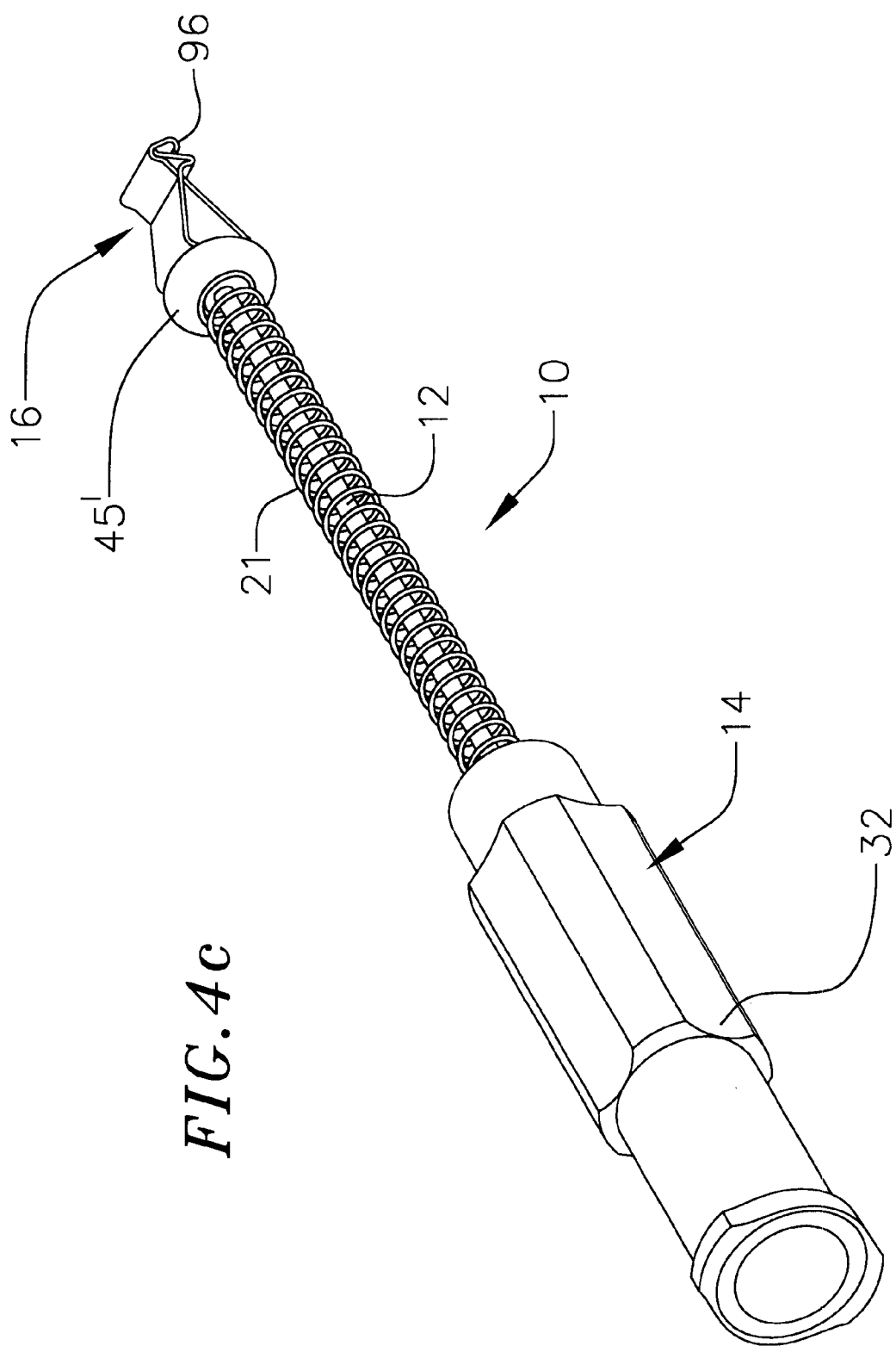
FIG. 4c is a semi-schematic perspective view of the hypodermic needle assembly of FIG. 4a shown in its activated state.

The present invention is directed to a hypodermic needle assembly designed such that the movement of the needle shield into position to block the needle tip occurs as a direct consequence of the depression of a syringe plunger while injecting a medicant into a patient.

One illustrative embodiment of a hypodermic needle assembly according to the present invention is shown in FIGS. 1a–1c. The hypodermic needle assembly 10 shown therein comprises an introducing needle 12 arranged within a needle hub 14 in a conventional manner, and a spring-loaded safety clip needle tip guard assembly 16. The spring-loaded safety clip assembly 16 is mounted around the shaft of the needle 12 and, in an unactivated mode (as shown in FIG. 1a), is positioned within the needle hub 14. The safety clip assembly 16 comprises a pressure trigger 18, a spring clip 20, and a resilient member 21 fixedly connected therebetween. The spring clip 20 is slidably mounted to the needle 12 within the needle hub 14.

Any suitable needle 12 can be utilized with the present invention such that the needle 12 is constructed to slidingly cooperate with the spring clip 20. In the embodiment shown in FIGS. 1a–1c, the needle 12 includes a hollow shaft having a sharp tip 22 at the distal end and a proximal end which is arranged within the needle hub 14. The proximal end of the needle 12 communicates with a syringe tip engagement chamber 42 defined by the needle hub 14 and described below in greater detail.

Referring to FIGS. 1a–6a, the needle 12 has a proximal end adjoining the needle hub 14 and a distal end having a sharp tip 22 and comprises a cylindrical shaft having a longitudinal axis and defining an inner hollow passageway having an inner diameter. A needle stop 24 is disposed along the length of the needle shaft between the proximal and distal ends and, preferably, is proximate to the distal end of the needle. The diameter of the hollow passageway (not shown) extending through the needle is substantially constant. In one preferred embodiment, the needle also has the same outside diameter along its entire length. In this embodiment, the needle stop 24 is a crimped portion of the needle 12 formed by crimping the needle utilizing any conventional needle crimping tool. According to this preferred embodiment, the needle stop 24 comprises a crimped portion of the needle that extends out of the longitudinal axis defined by the rest of the needle shaft. Preferably, the needle stop 24 extends about 0.002 inches outside of the initial outside diameter of the needle shaft 12 prior to crimping. In one embodiment the crimp is formed with a cylindrical crimping tool with a radius of about 0.118 inches.

Referring now to FIGS. 1b–4b, 5c, and 6b, the distance between the needle stop 24 and the needle tip 22 must be less than the total length of the spring clip 20 such that the needle tip 22 can be blocked thereby. In a preferred embodiment, the distance between the needle stop 24 and the needle tip is such that the needle stop engages a restraining hole or opening 26 in an end wall 28 of the spring clip 20 just after the spring clip engages to block the needle tip. Because the restraining opening 26 in the end wall 28 of the spring clip 20 in unable to move past the needle stop 24, the spring clip is prevented from being pulled from or otherwise being moved off the distal end of the needle 12. Thus, when the spring clip is activated such that it slides distally along the length of the needle 12 to the tip 22, the needle tip is blocked by the spring clip and the portion of the needle stop 24 extending out of the longitudinal axis of the needle 12 interacts with the restraining hole 26 in the end wall 28 to prevent the spring clip from being fully withdrawn from the needle 12, thus preventing the needle tip from being exposed.

Although one embodiment of a needle 12 is described above, any suitable needle can be utilized such that the needle can be easily inserted into and withdrawn from a patient, the spring clip 20 can readily slide along the needle, and the spring clip cannot be fully withdrawn from the needle once the spring clip is engaged on the needle tip.

Although a crimped needle stop 24, as described above, is preferable because of the simple and inexpensive nature of producing a crimp in a needle, the needle stop 24 can be formed in any shape suitable to prevent the spring clip 20 from being completely withdrawn from the needle tip 22. In one alternative embodiment, the needle stop 24 is provided as an enlarged diameter portion of the needle where the diameter is slightly larger than the diameter of the restraining opening 26 through the end wall 28 of the spring clip. Thus, when the spring clip is launched along the length of the needle by the resilient member 21, which in a preferred embodiment is a spring, and the needle tip 22 is blocked by the spring clip, the diameter of the needle stop 24 prevents the spring clip from being completely withdrawn from the needle tip 22, thereby preventing the needle tip from being exposed. Such an enlarged-diameter needle stop can be formed by any suitable technique, such as, for example, by electroetching material from the needle upstream and downstream from the needle stop area to reduce the diameter of the remainder of the needle. Grinding is another alternative for shaping the needle 12 to the desired configuration. Either technique provides a shaped needle 12 of integral construction, which is preferred. Other possible techniques for providing the needle stop include plating the area selected for enlargement, or insert molding a band of polymeric material around the needle or welding or adhesive bonding a sleeve onto the needle.

Any needle hub 14 design can be utilized in the safety hypodermic needle assembly of the present invention, such that a needle 12 and safety clip assembly 16 are arranged therein and, if separate, a syringe 30 comprising a plunger 31 incorporating an extension pin 31a which extends into the syringe tip and, in some embodiments, extends through and out from the syringe tip can be adjoined thereto. The needle hub 14 employed in accordance with the embodiments of the invention shown in FIGS. 1–6 comprises an integrally molded body 32 defining an axial cylindrical inner needle passageway 34 having dimensions designed to accept the needle 12 therein and to allow the pressure trigger 18 and resilient member 21 to be slidably movable therein. (In some embodiments, the reference numbers are followed by one or more superscript primes (') to differentiate between common elements which have different structural features.) With regard to the fixation of the needle 12 and pressure trigger 18 within the passageway 34, the needle hub 14 should meet the "pull strength standard" such that if the needle 12 should strike bone or solid mass during injection, neither the needle 12 nor pressure trigger 18 will be pushed proximally out from the back of the needle hub 14. The needle passageway 34 is also arranged and designed such that the slidable pressure trigger 18 cannot be moved distally beyond a certain point, nor can the needle 12 be dislodged from the needle hub 14 in a distal direction. Table 1, below lists international standards for needle hub "push" and "pull" strengths for needles having a variety of outer diameters.

TABLE 1

International Standard for Needle Hub Push and Pull Strengths

| Needle Outer Diameter (mm) | Connection Strength (N) |
| --- | --- |
| 0.3 | 22 |
| 0.33 | 22 |
| 0.36 | 22 |
| 0.4 | 22 |
| 0.45 | 22 |
| 0.5 | 22 |
| 0.55 | 34 |
| 0.6 | 34 |
| 0.7 | 40 |
| 0.8 | 44 |
| 0.9 | 54 |
| 1.1 | 69 |
| 1.2 | 69 |

A cylindrical spring clip cavity 36 coaxial with the needle passageway 34 and having a support wall 38 in its proximal end and a spring clip opening 40 in its distal end is provided in the distal end of the needle hub 14. The proximal end of the needle hub is defined by the syringe tip engagement chamber 42 which is slightly conical in shape and which, in some embodiments, is a female luer fitting. The syringe tip engagement chamber is coaxial with the needle passageway 34 and has an opening 44 provided therein to accommodate the tip of a syringe, which generally has a male luer configuration, in liquid-tight engagement. The spring clip 20, when unactivated, is positioned within the spring clip cavity 36. A pressure fitting 45 is located at the proximal end of the spring clip and is in mechanical communication with the support wall 38 of the spring clip cavity. The pressure trigger 18 and resilient member 21 are positioned within the needle passageway 34, such that the proximal end of the needle clip assembly 16 and the needle 12 are in mechanical and fluid communication, respectively, with the distal end of the syringe tip engagement chamber 42. As shown in FIGS. 1a–6a, the above elements are arranged such that the needle 12 passes at least partially through and out from the distal end portion of the pressure trigger 18, through the resilient member 21 in the needle passageway 34, through the spring clip 20 in the spring clip cavity 36, and out from the needle hub opening 40.

The needle hub 14, comprising the needle passageway 34, spring clip cavity 36, and syringe tip engagement chamber 42, can have any suitable design such that the needle 12, needle tip guard 16, pressure trigger 18 and syringe 30 can be functionally disposed therein. In the embodiment shown in FIGS. 1a–1c, for example, the distal needle hub exit opening 40 of the spring clip cavity is in coaxial arrangement with the needle passageway 34, and has a sufficient diameter to allow the spring clip 20 to be ejected distally from the needle hub 14 along the needle shaft 12. In this embodiment, the needle passageway 34 has an opening 46 in the spring clip cavity end wall 38, and the pressure fitting 45, which is ring-shaped and located at the proximal end of the spring clip and mounted around the needle, is frictionally engaged with the opening 46. The needle passageway 34 also has a pressure trigger engaging opening 48 arranged in the distal end portion of the syringe tip engagement chamber 42, such that a pressure trigger fitting portion 47 of the pressure trigger 18 is frictionally engaged therewith, and such that the pressure trigger can engage a pin 31a which is provided as an extension of the syringe plunger 31. In this embodiment, the needle passageway 34 also comprises a pressure trigger stop 49 comprising a metal sleeve. The sleeve incorporates a pressure trigger stop indented portion 49a formed therein which is arranged coaxially within the needle passageway 34 such that the pressure trigger 18 is prevented from sliding distally past the pressure trigger stop indention 49a. In addition, the pressure trigger engaging opening 48 at the proximal end of the needle passageway 34 is tapered such that the slidable pressure trigger 18 cannot be moved in the proximal direction. In this embodiment, the resilient member 21 is a coil spring disposed coaxially around the needle 12 within the needle passageway 34. The spring is engaged at its distal end in a circumferential recess in the pressure fitting 45 which, in turn, is in contact with the spring clip end wall 28 and is engaged at its proximal end with the pressure trigger 18, such that the spring mechanically interacts with both the spring clip and the pressure trigger. While in this embodiment, the spring is not fixedly attached to the pressure trigger 18, if desired, the spring may be fixedly attached thereto. The needle 12 is fixedly attached to the pressure trigger, such that when the pressure trigger is moved distally at the urging of the extension pin 31a of the syringe plunger 31, the needle also moves in the distal direction.

In the embodiment of the needle assembly shown in FIGS. 2a–2c, the needle passageway 34, spring clip cavity 36, and syringe tip engagement chamber 42 are designed generally as described for FIGS. 1a–1c above, except that the needle passageway 34 has dimensions sufficient to allow the insertion of a pressure trigger 18' that extends along the entire length of the needle passageway 34. The proximal end of the pressure trigger 18' interacts with the extension pin portion 31a of the plunger 31 of the syringe 30 and the distal end portion of the pressure trigger 18' interacts directly with the pressure fitting 45 disposed in the distal end of the needle passageway 34 adjacent to the proximal end of the spring clip cavity 36. In such an embodiment, the resilient member 21 is a coil spring disposed coaxially around the needle 12 within the cylindrical body of the pressure trigger 18'. As was the case with the FIG. 1 embodiment, the spring is engaged at its distal end in a circumferential recess in the pressure fitting 45 which, in turn, is in contact with the spring clip end wall 28. In this embodiment, the needle passageway 34 also includes a pressure trigger stop 49' comprising a metal sleeve having an indented portion 49a' therein arranged coaxially within the needle passageway 34 and designed to interact with an enlarged portion 18a' of the pressure trigger such that the pressure trigger 18' is prevented from sliding distally past the pressure trigger stop 49a'. The pressure trigger engaging opening 48 at the proximal end of the needle passageway 34 is also tapered, as shown, such that the slidable pressure trigger 18' cannot be moved in the proximal direction. In this embodiment, as in the embodiment shown in FIGS. 1a–1c, the needle 12 is fixedly attached to the slidable pressure trigger 18' such that the needle 12 moves therewith when the pressure trigger 18' is urged distally by the action of the syringe plunger 31.

Although metal sleeves 49 and 49' are shown forming the pressure trigger stop 49a and 49a' in the two exemplary embodiments shown in FIGS. 1a–1c and 2a–2c respectively, in an alternative embodiment the metal sleeve is omitted and the pressure trigger stop 49a is provided by a ring integrally formed circumferentially around the wall of the needle passageway 34 which extends into the needle passage, reducing its diameter at that location.

In the exemplary embodiment of the needle assembly shown in FIGS. 3a–3c, the spring clip assembly 16 further comprises a spring clip housing 50. In this embodiment, the spring clip cavity 36 has dimensions such that the housing 50 can be inserted into the cavity and then ejected distally therefrom along the needle shaft 12. In this embodiment, as is best shown in FIGS. 3a and 3b, the needle passageway 34 has a needle clip housing engaging opening 46' formed in the spring clip cavity end wall 38. A pressure fitting 51, which is integrally formed on the proximal end of the housing 50, is frictionally engaged in the opening 46'. A frangible seal 48', which is formed around an external flange 47' disposed around the proximal end of the pressure trigger 18", is annularly engaged with the inside surface of the wall of the syringe tip engagement chamber 42. In this embodiment, as with the embodiment shown and described in FIGS. 1 and 2 above, the needle passageway 34 comprises a pressure trigger stop 49a" comprising a ring formed integrally in the wall of the needle passageway 34 and arranged such that the pressure trigger 18" is prevented from sliding distally past the pressure trigger stop 49a". If desired, in an alternative embodiment of the spring assembly of the present invention, a portion of the proximal end of the needle passageway 34 can be tapered such that the slidable pressure trigger 18" cannot be moved in the proximal direction due to an interference between the taper and the external flange 47'.

In the embodiment shown in FIGS. 3a and 3b, the pressure trigger 18" comprises a cylindrical body within which the needle 12 is fixedly attached and the resilient member 21 is disposed. The resilient member 21 is a coil spring and is disposed coaxially around the needle 12 within the body of the pressure trigger 18", which itself is disposed within the needle passageway 34. In the unactivated state (shown in FIG. 3a), the external flange 47' extends outwardly from the pressure trigger 18" and engages the inner wall of needle passageway 34 at the frangible seal 48' formed around the inner wall. When engaged by the extension pin 31a of the plunger 31 and the plunger is pushed in the distal direction, the frangible seal 48' is broken and the pressure trigger 18" can slide distally in the needle passageway (FIG. 3b). The needle 12 is fixedly attached at its proximal end to the pressure trigger 18", and the spring 21 extends between the pressure trigger 18" and the housing 50, such that the spring mechanically interacts with both the spring clip 20 and the pressure trigger 18". As in the embodiment shown in FIGS. 2a–2c, the pressure trigger 18" in this embodiment is of sufficient length such that the proximal end of the pressure trigger 18" mechanically interacts with the extension pin 31a of the syringe plunger 31, and the distal end of the pressure trigger 18" mechanically interacts directly with the proximal end of the housing 50. In this embodiment, the above elements are arranged such that the needle 12 passes through the pressure trigger 18", and the spring 21 in the needle passageway 34, through the housing 50 and spring clip 20 in the spring clip cavity 36, and out from the needle hub opening 40.

In the exemplary embodiment of the needle assembly shown in FIGS. 4a–4c, the spring clip pressure fitting 45' has a relatively wider diameter so as to effectively reduce the support wall 38' of the needle tip guard cavity 36 to a minimum. In this embodiment, the pressure trigger 18''' further comprises an annular stop engaging flange or skirt 49b which extends around the proximal end of the pressure trigger with a diameter slightly larger than the diameter of the cylindrical pressure trigger body 18'''. The needle passageway 34 also comprises a pressure trigger stop 49a''' comprising a ring formed circumferentially around the wall defining the needle passageway 34 thereby reducing the diameter of the needle passageway at that location. The pressure trigger 18''' is prevented from sliding distally past the pressure trigger stop 49a''' by the engagement of the stop 49a''' with the flange 49b. In addition, a ring 48'' extending around the proximal end of the inner surface of the needle passageway 34 is configured to engage the stop engaging flange 49b such that the slidable pressure trigger 18''' cannot be moved past the ring 48'' in the proximal direction.

In this embodiment, the pressure trigger 18''' comprises a slidable cylindrical body within which the needle 12 is fixedly attached and the resilient member 21 is disposed. The resilient member 21 is a coil spring and is disposed coaxially around the needle 12 within the body of the pressure trigger 18''', which itself is disposed within the needle passageway 34. The needle is fixedly attached at its proximal end to the pressure trigger 18'''. In this embodiment, the spring is not fixedly attached to the pressure fitting but is in removable contact therewith and mechanically interacts with both the spring clip 20 and the pressure trigger 18'''. The needle 12 extends proximally from the pressure trigger 18''' such that the proximal end of the needle 12 mechanically interacts with the extension pin 31a of the plunger 31 of the syringe 30, and the distal end of the pressure trigger 18''' mechanically interacts directly with the pressure fitting 45'. In the illustrated embodiment, the needle 12 passes through the pressure trigger 18''' and spring 21 of the needle tip guard assembly 16 in the needle passageway 34, through the pressure fitting 45' and spring clip 20 in the spring clip cavity 36, and out from the needle hub opening 40. In this embodiment, the clip 20 extends distally from the cavity 36 when the needle assembly is in its unactivated condition.

Figure 5A:
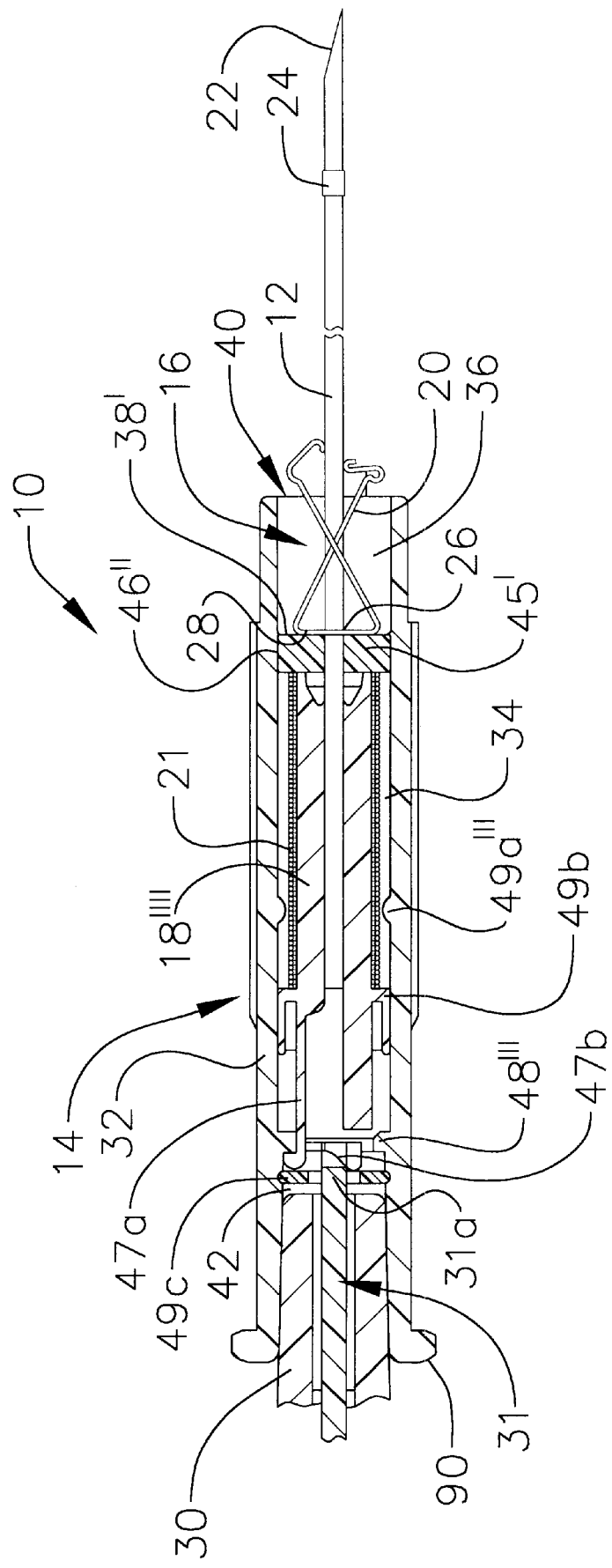
FIG. 5a is a semi-schematic cross-sectional top view of an unactivated hypodermic needle assembly according to a fifth embodiment of the present invention attached to a syringe.

In the exemplary embodiment shown in FIG. 5a, the needle clip assembly 16 and the needle hub 14 are generally as described above with reference to FIGS. 4a–4c, except that the syringe tip engagement chamber 42 further comprises a proximal needle stop 49c and the pressure trigger 18'''' further comprises at least one flexible hook 47a. The flexible hook 47a is configured to engage the proximal needle stop 49c to thereby prevent the pressure trigger from sliding proximally out of the needle hub 14 when it is subjected to a proximally directed force; such as, for example, when the needle impacts on a bone. The proximal needle stop 49c may comprise any suitable engaging flange, such as, for example, a snap ring disposed within an annular groove formed in the wall of the syringe tip engagement chamber 42. In this embodiment, the engaging opening 48''' comprises an engaging surface specifically configured to catch and hold the flexible hook 47a to releasably hold the pressure trigger 18'''' against inadvertent distal movement prior to activation by the syringe extension pin 31a. The hook 47a is configured such that, during activation, the syringe extension pin 31a interacts with a platform 47b which extends from the bottom portion of the hook to move the hook inwardly, thereby disengaging the hook from the opening 48''' and allowing distal movement of the pressure trigger 18''''. In such an embodiment, once the hook 47a on the pressure trigger 18'''' is moved distally past the engaging opening 48''', the hook 47a springs outwardly toward the wall of the needle passageway 34. When in this configuration (shown in FIG. 5c), any proximal movement of the pressure trigger 18'''' will push the hook 47a against the annular distal wall of the engaging opening 48''' to thereby block further proximal movement. As in the embodiments shown and described in FIGS. 1–4 above, the needle 12 is fixedly mounted within the slidable pressure trigger 18'''' such that the needle moves with the pressure trigger when the pressure trigger is moved distally by the extension pin 31a of the syringe plunger 31.

Figure 5B:
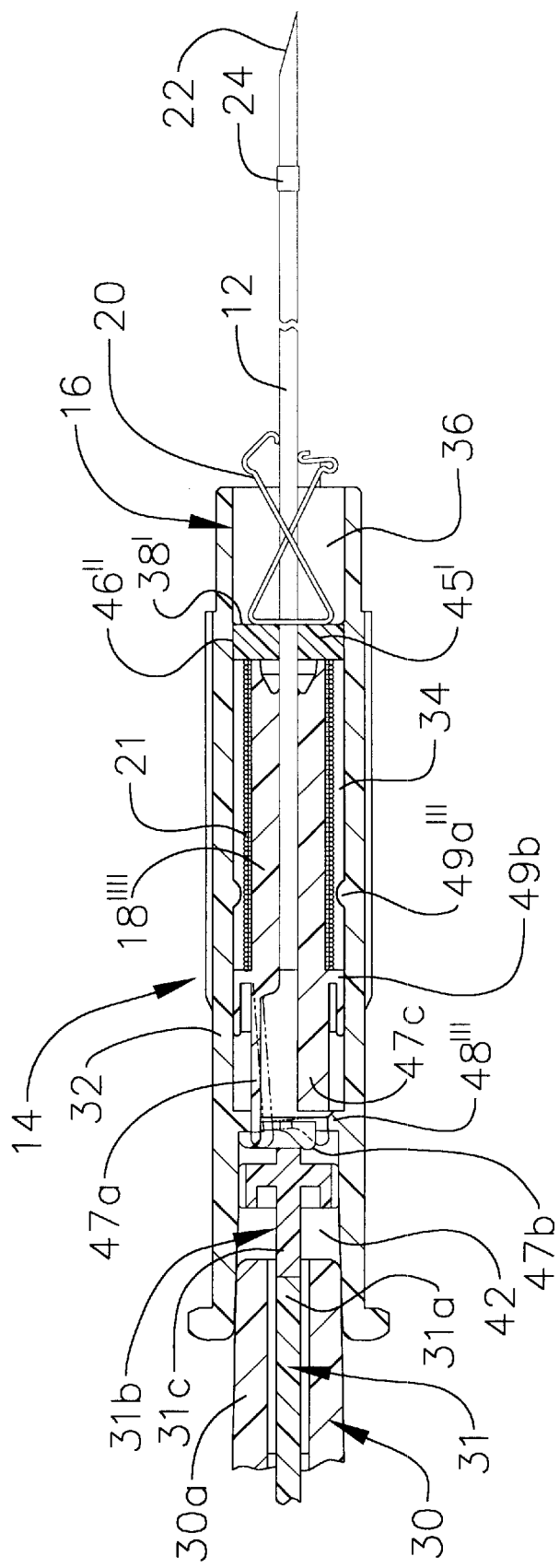
FIG. 5b is a semi-schematic cross-sectional top view of an unactivated hypodermic needle assembly according to the sixth embodiment of the present invention attached to the syringe.
Figure 5C:
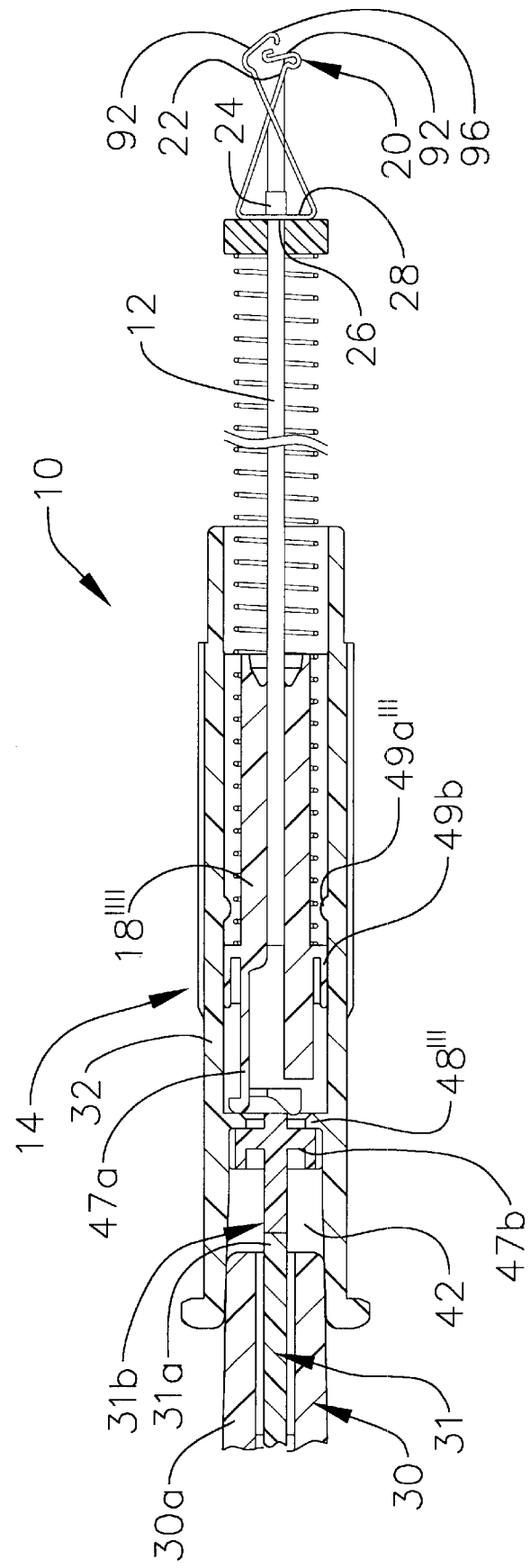
FIG. 5c is a semi-schematic top view of the hypodermic needle assembly of FIG. 5b shown in its activated state and attached to a syringe.

In the exemplary embodiment shown in FIGS. 5b and 5c, the needle tip guard assembly 16 and the needle hub 14 are generally as described above with reference to FIGS. 4a–4c and 5a, except that the assembly further comprises an intermediate pusher assembly 31b disposed within the syringe tip engagement chamber 42 between the syringe 30 and the pressure trigger 18''''. In this embodiment the pressure trigger 18'''' comprises at least one flexible hook 47a and further has an enlarged proximal end 47c. The intermediate pusher assembly 31b is configured to transmit the force of the extension pin 31a of the syringe plunger 31 to the pressure trigger 18''''. The enlarged proximal end 47c is configured to engage the opening 48''' such that the pressure trigger 18'''' is prevented from sliding proximally out of the needle hub 14 when subjected to a proximally directed force, such as, for example a needle impact on a bone. The intermediate pusher assembly 31b has an elongated pin or arm 31c on its proximal end, which is designed and arranged to extend into the tip 30a of the syringe 30 to engage the extension pin 31a. Thus, in this embodiment, the extension pin 31a needs to extend only to essentially the opening of the syringe tip and does not need to extend therefrom as is shown in the previously described embodiments.

In this embodiment, the engaging opening 48''' further comprises a proximal facing annular engaging surface configured to engage the flexible hook 47a which, in turn, releasably holds the pressure trigger 18'''' to prevent inadvertent distal movement of the pressure trigger prior to activation by the pusher assembly 31b. As best shown in phantom in FIG. 5b, the hook 47a is configured such that during activation, the intermediate pusher assembly 31b interacts with the platform 47b to move the hook 47a inwardly to disengage the hook from the engaging opening 48''' to thereby allow distal movement of the pressure trigger 18''''. As is best seen in FIG. 5c, after the device is activated and the hook 47a is moved distally past the engaging opening 48''', the hook springs outwardly toward the wall of the needle passage 34. When the syringe assembly is in this activated state, proximal movement of the pressure trigger 18'''' will push the hook 47a against the distal facing annular wall of the engaging opening 48''', thereby stopping further proximal movement of the pressure trigger. As in the embodiments shown and described in FIGS. 1–4 above, the needle 12 is fixedly mounted within the slidable pressure trigger 18'''' such that the needle 12 moves with the pressure trigger when the pressure trigger is moved distally by the intermediate pusher assembly 31b.

Turning to FIGS. 6a–6e, yet another embodiment of a safety hypodermic assembly provided in accordance with the practice of the present invention is shown. In this embodiment, the needle 12 is fixedly attached to the needle hub 14' by means of an inner needle assembly 52. The needle assembly 52 is integral with the needle hub 14' and is arranged in the needle passageway 34 such that the needle 12 does not move with respect to the needle hub 14' when the needle clip assembly 16 is activated. In this embodiment, the needle 12 is fixedly attached to the inner needle mounting assembly 52 by a glue or adhesive plug 56 which is formed by injecting glue into the mounting assembly 52 through an opening 58 (shown in FIG. 6d) disposed through the outer surface of the needle hub 14'. As best shown in FIG. 6b, two passages 60a and 60b extend along the sides of the inner needle mounting assembly 52, such that a pressure fitting 45'' can extend therethrough and mechanically engage the pressure trigger 18''''.

As shown in FIGS. 6c and 6d, the pressure fitting 45'' of this embodiment comprises an elongated body 66 having a bifurcated proximal end forming two elongated arms 68a and 68b and a cylindrical distal end 70 defining a cavity 72. The cavity 72 is configured to enclose the distal end of the inner needle assembly 52 and the resilient member 21 which (as shown in FIG. 6a), is disposed about the distal end of the inner needle assembly 52. The arms 68a and 68b are designed and arranged such that they extend through the passages 60a and 60b (FIG. 6b) in the needle hub 14' and mechanically engage the distal end of the pressure trigger 18'''' when the needle assembly is in its unactivated condition. In the embodiment shown in FIGS. 6a–6e, the resilient member 21 is a coil spring and is disposed coaxially around the needle assembly 52 within the body of the pressure fitting 45'', which itself is disposed within the needle passageway 34. As in the previous embodiments, the spring 21 is in contact with and may be fixedly attached at its distal end to the pressure fitting 45'' such that it mechanically interacts with the spring clip 20. In the preferred embodiment, the distal end of the pressure fitting 45'' comprises most of the proximal wall of the spring clip cavity 36. In such an embodiment, as is best shown in FIGS. 6a and 6b, the needle passageway 34 has an enlarged opening 46''' which engages the enlarged distal end of the pressure fitting 45''. As shown best in FIGS. 6a and 6b, in this embodiment the pressure fitting 45'' is designed such that when the resilient member 21 pressingly launches the pressure fitting 45'', after the release of the pressure fitting 45'' from the engaging opening 46''', the entire pressure fitting is launched along with the spring clip distally along the needle 12 and covers a substantial portion of the needle 12.

Turning to FIGS. 6a and 6d, the pressure trigger 18'''' comprises a substantially cylindrical body 74 having a proximal cylinder wall 76 defining a proximal cavity 78 and a distal cylindrical wall 80 defining a distal cavity 82. In this embodiment, the proximal end of the pressure trigger 18'''' comprises a plunger engaging portion or arm 86 extending along the central axis from within the proximal cavity 78 of the pressure trigger. The arm is in the shape of a pin and is sufficiently elongated that it extends some distance into the opening of the syringe tip. Thus, to contact the end of the pressure trigger 18'''', the extension pin 31a of the syringe needs to extend only part way to the opening of the syringe tip and does not need to extend therefrom.

As shown in FIGS. 6a, 6b, and 6e, the inner needle assembly 52 is formed integrally with the needle hub 14' and is arranged such that the distal cylindrical wall 80 of the pressure trigger 18'''' engages the needle assembly 52 and thereby provides a fluid path seal. Turning to FIG. 6e, an enlarged section 52a of the needle assembly 52 extends completely across the width of the needle hub 14' and is integrally formed therewith. In this embodiment, the distal cylindrical wall 80 of the pressure trigger 18'''' can only move distally to the stop 81 of the needle assembly 52, thus limiting its distal movement. The step between the needle passageway 34 and the engaging opening 46'''' engages the enlarged distal end of the pressure fitting 45'' to thereby prevent the pressure fitting from being moved in the proximal direction.

In the embodiment shown in FIGS. 6a–6e, the pressure trigger 18'''' is also designed to provide fluid communication between the syringe tip engagement chamber 42 and the proximal end of the needle 12. To provide such fluid communication, an opening 88 is provided in the proximal cavity 78 of the pressure trigger 18'''' which defines a fluid passageway between the proximal cavity 78 and the distal cavity 82. The distal cavity 82 is designed and arranged such that the proximal end of the inner needle assembly 52 having the proximal end of the needle 12 disposed therein, extends inside the distal cavity 82. The distal wall 80 of the pressure trigger 18'''' is in turn sealingly engaged around the proximal end of the inner needle assembly 52, such that a tight seal is formed therebetween. Accordingly, fluid introduced into the syringe tip engagement chamber 42 flows into the proximal cavity 78 through the opening 88 into the distal cavity 82 and thereby into the needle 12.

Although one specific arrangement of the embodiment of FIG. 6 is described above, any suitable design may be utilized such that the following design elements are incorporated therein: 1) the needle 12 is fixedly attached to the outer needle hub 14' such that the needle does not move when the needle clip assembly 16 is activated; 2) the pressure fitting 45'' comprises an elongated body within which the needle and the resilient member 21 are disposed; 3) the pressure trigger 18'''' has an arm or pin on its proximal end of sufficient length such that the proximal end mechanically interacts with the extension pin 31a of the plunger 31 of the syringe 30 and the pressure trigger distal end mechanically interacts with the pressure fitting 45 and 4) the above elements are arranged such that the needle 12 passes out from the distal end of the pressure trigger 18'''', through the inner needle hub assembly 52 and the resilient member 21 in the needle passageway 34, through the pressure fitting 45'' and spring clip 20 in the spring clip cavity 36, and out from the distal needle hub opening 40.

As shown in the embodiments of the needle assembly described above with reference to FIGS. 1–6, the outer body 32 of the needle hub 14 is designed to facilitate manipulation of the needle hub 14 between the thumb and finger, for example, each end of the side walls may include a stepped portion or textured surface to facilitate gripping. In addition, in a preferred embodiment, the needle hub body 32 is made, for example, by injection molding a transparent material such as polypropylene, so that an ultraviolet light cured adhesive can be used to bond the needle 12 to the inner needle assembly 52. The other components of the needle assembly, such as the various embodiments of the pressure trigger, the pressure fitting, the inner needle mounting assembly, and the spring clip housing, can also be formed from polypropylene by injection molding. If desired, the needle hub and the pressure trigger of the FIG. 3 embodiment, which incorporate a frangible seal formed between the pressure trigger flange and the syringe engagement chamber wall, can be formed by injection molding polystyrene. In embodiments of the invention in which the syringe 30 is a separate device which can be detachably attached to the needle hub 14, the proximal end of the needle hub 14 can optionally include attaching means, such as, for example, a frictional fitting or a luer lock 90, as shown in FIGS. 1–6.

The blocking portion of the needle guard 16 itself can comprise any device suitable to safely block the tip 22 of the needle 12. As shown in FIGS. 1–6, in a preferred embodiment of the safety needle assembly of the present invention, the blocking portion of the needle guard 16 comprises an interlocking spring clip 20. Turning particularly to FIG. 1b, the spring clip 20 comprises elongated tensioning arms 92 which extend distally from the end wall 28 of the clip along the needle shaft 12. Two inwardly extending transverse wall portions 94a and 94b of the spring clip, having generally L-shaped extensions with curled lips on their ends, extend from the elongated arms 92 and project inwardly toward the longitudinal axis of the needle. In this embodiment, the transverse wall portions 94a and 94b, which are continuously resiliently urged towards the longitudinal axis by the action of the spring clip 20 design, are provided to engage the needle, such that the clip cannot be moved in a proximal direction. The end wall 28 of the spring clip 20 has a restraining opening 26 disposed therein to allow the needle 12 to pass therethrough. The restraining opening has a diameter which allows the spring clip 20 to slidingly move along the shaft of the needle 12 at the resilient urging of the spring 21, but when the clip has arrived near the needle tip, the opening engages the extended portion of the needle stop 24 to thereby prevent the clip 20 from being completely withdrawn from the needle tip 22. One embodiment of a spring clip useful in accordance with practice of the present invention is disclosed in U.S. Pat. No. 6,117,108, which is incorporated herein in its entirety by this reference.

In the embodiment of the safety hypodermic needle assembly provided in accordance with the practice of the invention shown in FIGS. 3a–3c, the spring clip 20 is substantially identical to the spring clip 20 described above and shown in FIGS. 1a–1c and 2a–2c. However, turning particularly to FIG. 3b, in this embodiment, the spring clip 20 is positioned inside the spring clip housing 50 which comprises proximal and distal needle openings 98a and 98b arranged such that the needle 12 can extend therethrough. The needle tip guard 16 of this embodiment is designed such that the needle tip 22 enters both the housing 50 and the needle tip spring clip 20. However, the spring clip 20 operates as described above, wherein the transversely biased spring arms 92 and associated transverse wall portions 94a and 94b engage to block the needle tip 22, and the restraining opening 26 in the end wall 28 is biased against needle stop 24 by the spring 21. In such an embodiment, it should be understood that the spring clip 20 may function to completely block the needle tip 22, even in the absence of the housing 50, and in fact the housing 50 may be designed such that it can be easily detached from the spring clip.

Although only one embodiment of the spring clip 20 is described above, it should be understood that any suitable spring clip design may be utilized, such that the spring clip operates to block the needle tip 22 via two separate mechanisms. Turning to FIGS. 1b–6b, for example, in one mechanism, the arms 92 of the spring clip 20 are designed to engage such that they block the needle tip 22 from being moved in a distal direction relative to the spring clip. In the second mechanism, the restraining opening 26 in the end wall 28 of the spring clip is designed such that the enlarged portion of the needle stop 24 engages therewith and thus prevents the needle 12 from being moved in the proximal direction relative to the spring clip. The spring clips disclosed herein are preferably of integral construction, and made from stainless steel or other suitable material having the necessary memory and spring characteristics.

During operation, the hypodermic needle assembly 10, either as an integral syringe unit or, preferably, as an attachment mounted over a separate syringe 30, as shown in any of FIGS. 1b–6b, is grasped by the user on the outer body 32 of the needle hub 14. The assembly 10 is oriented such that the needle tip 22 is positioned against the patient's skin. The needle 12 is then inserted into the patient. When the needle has successfully penetrated the patient, the syringe plunger 31 is urged distally forward, such that any fluids contained in the syringe are forced into the needle 12 in fluid communication therewith, in substantially the same way that conventional hypodermic needle syringes are used. Specifically, the needle hub 14 is utilized to position the needle 12 a selected distance into the patient and then the syringe plunger 31 is used to inject the desired medicants. As shown best in FIGS. 1b–6b, during this operation and during the injection, the needle tip guard assembly 16 remains unactivated because the elongated extension pin 31a on the syringe plunger mechanically activates the pressure trigger 18 only after substantially all of the medicant has been injected.

When the medicant has been fully delivered, the syringe plunger extension pin 31a mechanically interacts with the pressure trigger (either by direct contact with the pressure trigger or through another structure). As the distal movement of the extension pin 31a applies a distally directed force on the pressure trigger, the engagement between the pressure trigger and the needle passageway is overcome, and the pressure trigger slides in a distal direction through the needle passageway. The movement of the slidable pressure trigger is then communicated to the associated pressure fitting, thereby disengaging the pressure fitting from the frictional engaging opening in the end wall of the spring clip cavity. This disengagement allows the compressed spring to resiliently urge the spring clip distally along the needle through the distal opening of the spring clip cavity and toward the needle tip. The spring clip moves along the needle until the arms of the spring clip move past the needle tip and are thereby free to spring closed, thereby blocking the distal path of the needle tip. Further distal movement of the spring clip is prevented by the interaction of the restraining opening in the end wall of the spring clip with the needle stop on the needle shaft or by any other suitable mechanism, such as, for example, a tether attaching the spring clip to the needle hub. In this position, the needle tip is prevented from re-emerging due to being shielded by the transverse portion of the spring clip, which forms a wall blocking the distal exit path of the needle tip, and the clip cannot be pulled off of the needle tip because of the engagement of the restraining opening with the needle stop. As is described below in detail, the spring clip can be engaged around the needle tip in a number of ways, according to the illustrative embodiments of the needle assembly of the present invention.

First, in the embodiment shown in FIGS. 1a–1c, the syringe plunger 31 is depressed, such that the extension pin 31a extends into the syringe tip engagement chamber 42 and out from the syringe tip. In this condition, the extension pin 31a engages the pressure trigger 18 that is frictionally held by the pressure trigger engaging opening 48 in the proximal end of the needle passageway 34. As the plunger presses against the pressure trigger 18, the pressure trigger and the needle 12 attached thereto are pushed in a distal direction through the needle passageway 34. The movement of the pressure trigger is transmitted through the compressed spring 21, to the spring clip pressure fitting 45 disposed within the spring clip engaging opening 46 in the distal end of the needle passageway 34. When the spring clip pressure fitting is urged out of the spring clip engaging opening, the compressed spring expands distally and urges the spring clip 20 out of the spring clip cavity 36 and distally along the needle 12 around which the spring clip is arranged. The spring clip and pressure fitting move along the length of the needle 12 until the needle stop 24 engages the restraining opening 26 in the end wall 28 of the spring clip. As shown in FIGS. 1b and 1c, when the spring clip 20 reaches the end of needle, such that the needle shaft 12 is no longer interposed between the lips 96 at the ends of the spring clip arms 92, the arms move by resilient action into the guard position blocking the needle tip 22. Retention of the spring clip guard on the needle in this position is ensured by the interlocking engaging arms 92 which prevent movement of the guard in the proximal direction and by the restraining opening 26 engaged with the needle stop 24 which prevents movement of the guard in the distal direction.

FIGS. 2a–2c show a second mechanism for engaging the needle tip guard assembly 16. In this embodiment, the plunger 31 is depressed, such that the extension pin 31a extends into the syringe tip engagement chamber 42 and out from the syringe tip. In this condition, the extension pin 31a engages the proximal end of the pressure trigger 18' which is frictionally held by the pressure trigger pressure fitting 47 in the pressure trigger engaging opening 48 in the proximal end portion of the needle passageway 34. As the plunger presses against the pressure trigger, the pressure trigger and the needle attached thereto are pushed in a distal direction through the needle passageway. The distal movement of the pressure trigger 18' is directly transmitted to the spring clip pressure fitting 45, which is in mechanical communication therewith, and which is disposed within the spring clip engaging opening 46 in the distal end of the needle passageway 34. When the spring clip pressure fitting 45 is urged out of the spring clip engaging opening 46, the compressed spring 21 expands distally and urges the spring clip 20, which can be fixedly attached to the pressure fitting, out from the spring clip cavity 36 distally along the needle 12 around which the spring clip 20 is arranged. The spring clip and pressure fitting move along the length of the needle 12 until the needle stop 24 engages the restraining opening 26 in the end wall 28 of the spring clip. As shown in FIGS. 2b and 2c, when the spring clip 20 reaches the end of needle such that the needle shaft 12 is no longer interposed between the lips 96 at the end of the spring clip arms 92, the arms move by resilient action into the guard position blocking the needle tip 22. Retention of the spring clip guard on the needle 12 in this position is ensured by the interlocking engaging arms 92 which prevent movement of the guard in the proximal direction and by the restraining opening 26 engaged with the needle stop 24 which prevents movement of the guard in the distal direction.

FIGS. 3a–3c show a third mechanism for engaging the needle tip guard assembly 16. In this embodiment, the syringe plunger 31 is depressed such that the extension pin 31a extends into the syringe tip engagement chamber 42 and out from the syringe tip. In this condition, the extension pin 31a engages the pressure trigger 18" held annularly by a frangible breakpoint or seal 48', which is annularly engaged with the inside surface of the wall of the syringe tip engagement chamber 42. As the plunger presses against the pressure trigger 18", the frangible seal 48' is broken and the pressure trigger and the needle 12 attached thereto are pushed in a distal direction through the needle passageway 34. The movement of the pressure trigger 18" is directly transmitted to the housing pressure fitting 51, which is in mechanical communication therewith and which is disposed within the housing engaging opening 46' in the distal end of the needle passageway 34. When the housing pressure fitting 51 is urged out of the housing engaging opening 46', the compressed spring 21 expands distally and urges the housing 50 and the spring clip 20 out of the spring clip cavity 36 distally along the needle 12 around which the housing and spring clip are arranged. The housing 50 and spring clip 20 move along the length of the needle 12 until the needle stop 24 engages the restraining opening 26 in the end wall 28 of the spring clip 20. As is shown in FIGS. 3b and 3c, when the spring clip 20 reaches the end of needle such that the needle shaft 12 is no longer interposed between the lips 96 at the end of the spring clip arms 92, the arms move by resilient action into the guard position blocking the needle tip 22. Retention of the spring clip 20 on the needle 12 in this position is ensured by the interlocking engaging arms 92 which prevent movement of the guard in the proximal direction and by the restraining opening 26 engaged with the needle stop 24 which prevents movement of the guard in the distal direction.

FIGS. 4a–4c show a fourth mechanism for engaging the needle tip guard assembly 16. In this embodiment, the syringe plunger 31 is depressed such that the extension pin 31a extends into the syringe tip engagement chamber 42 and out from the syringe tip, such that the extension pin 31a engages the proximal end of the needle 12. As the extension pin 31a presses against the proximal end of the needle, the pressure trigger 18''' and the needle attached thereto are pushed in a distal direction through the needle passageway 34. The movement of the pressure trigger 18''' is directly transmitted to the pressure fitting 45' which is in mechanical communication therewith and which is disposed within the engaging opening 46" in the distal end of the needle passageway 34. When the pressure fitting 45' is urged out of the engaging opening 46", the compressed spring 21 expands distally and urges the spring clip 20 out of the spring clip cavity 36 distally along the needle 12. The pressure fitting 45' and spring clip 20 move along the length of the needle 12 until the needle stop 24 engages the restraining opening 26 in the end wall 28 of the spring clip 20. As shown in FIGS. 4b and 4c, when the spring clip 20 reaches the end of needle, such that the needle shaft 12 is no longer interposed between the lips 96 at the end of the arms 92 of the spring clip, the arms move by resilient action into the guard position blocking the needle tip 22. Retention of the spring clip 20 on the needle 12 in this position is ensured by the interlocking engaging arms 92 which prevent movement of the guard in the proximal direction and by the restraining opening 26 engaged with the needle stop 24 which prevents movement of the guard in the distal direction.

FIG. 5a shows a fifth mechanism for engaging the needle tip guard assembly 16. In this embodiment, the activation mechanism is generally as described above with reference to FIGS. 4a–4c, except that the pressure trigger 18'''' further comprises at least one flexible hook 47a designed to engage the engaging opening 48'''. Accordingly, the needle guard activation process begins as before, where the syringe plunger 31 is depressed such that the syringe extension pin 31a extends into the syringe tip engagement chamber 42 and out from the syringe tip to thereby engage the engaging platform 47b of the pressure trigger 18''''. As the plunger extension pin 31a presses against the platform 47b, the flexible hook 47a is pressed inwardly such that it disengages from the engaging opening 48''', and the pressure trigger 18'''' and needle 12 attached thereto are pushed in a distal direction through the needle passageway 34. The movement of the pressure trigger 18'''' is directly transmitted to the pressure fitting 45' which is in mechanical communication therewith, and which is disposed within the engaging opening 46'' in the distal end of the needle passageway 34. When the pressure fitting 45' is urged out of the housing engaging opening 46'', the compressed spring expands distally and urges the spring 21 and the spring clip 20 out of the spring clip cavity 36 distally along the needle 12. The pressure fitting 45' and the spring clip 20 move along the length of the needle 12 until the needle stop 24 engages the restraining opening 26 in the end wall 28 of the spring clip 20. As was the case with the embodiment of FIGS. 4a–4c, when the spring clip 20 reaches the end of the needle such that the needle shaft is no longer interposed between the lips at the end of the arms of the spring clip, the arms move by resilient action into the guard position blocking the needle tip 22. Retention of the spring clip on the needle in this position is ensured by the interlocking engaging arms which prevent movement of the guard in the proximal direction and by the restraining opening 26 engaged with the needle stop 24 which prevents movement of the guard in the distal direction. In this embodiment the pressure trigger 18'''' is prevented from moving distally past the needle stop 49a''' by the engagement of the annular stop flange 49b and is prevented from moving proximally past the needle stop 49c when unactivated, and past the opening 48''' when activated, by the flexible hook 47a.

FIG. 5b shows a sixth mechanism for engaging the needle tip guard assembly 16. In this embodiment, the activation mechanism is generally as described above with reference to FIG. 5a, except that the assembly further comprises an intermediate pusher assembly 31b. Accordingly, the needle guard activation process begins by depressing the plunger 31 such that the extension pin 31a extends into the syringe tip which is mounted in the syringe tip engagement chamber 42. The pin 31a engages the elongated pin or arm 31c of the intermediate pusher assembly 31b which extends into the open syringe tip and thereby communicates the distal motion of the plunger to the engaging platform 47b of the pressure trigger 18''''. As the intermediate plunger assembly 31b presses against the platform 47b, the flexible hook 47a is pressed inwardly such that it disengages from the engaging opening 48''' (as shown in phantom in FIG. 5b), and the pressure trigger 18'''' and the needle 12 attached thereto are pushed in a distal direction through the needle passageway 34. The movement of the pressure trigger 18'''' is directly transmitted to the pressure fitting 45' which is in mechanical communication therewith and which is disposed within the engaging opening 46'' in the distal end of the needle passageway 34. The pressure fitting 45' is thereby urged out of the housing engaging opening 46'', and the compressed spring 21 expands distally and urges the pressure fitting 45' and the spring clip 20 out of the spring clip cavity 36 distally along the needle 12. Turning to FIG. 5c, when the spring clip 20 reaches the end of the needle such that the needle shaft 12 is no longer interposed between the lips 96 at the end of the arms 92 of the spring clip, the arms move by resilient action into a guard position blocking the needle tip 22. Retention of the spring clip 20 on the needle 12 in this position is ensured by the interlocking engaging arms 92 which prevent movement of the guard in the proximal direction and by the restraining opening 26 engaged with the needle stop 24 which prevents movement of the guard in the distal direction. In this embodiment, the pressure trigger 18'''' is prevented from moving distally past the needle stop 49a''' by the engagement of the annular stop flange 49b and is prevented from moving proximally past the opening 48''', once activated, by the flexible hook 47a.

FIGS. 6a–6d show a seventh mechanism for engaging the needle tip guard assembly 16. In this embodiment, the plunger 31 engages the pressure trigger 18''''' which has a plunger engaging portion or arm 86 which extends into the opening at the tip of the syringe 30. As the plunger presses against the pressure trigger 18''''', the pressure trigger is pushed in a distal direction through the needle passageway 34 and against the pressure trigger fitting 45''. The movement of the pressure trigger 18''''' is directly transmitted to the pressure fitting 45'' which has an enlarged distal end portion disposed in and frictionally engaged in the opening 46''' in the distal end of the needle passageway 34. In this embodiment, the needle 12 itself does not move relative to the needle passageway 34. When the enlarged distal end of the pressure fitting 45'' is urged out from the housing engaging opening 46''', the compressed spring 21 expands distally and urges the spring clip 20 out of the spring clip cavity 36 distally along the needle 12. The pressure trigger 18''''' and spring clip 20 move along the length of the needle 12 until the needle stop 24 engages the restraining opening 26 in the end wall 28 of the spring clip. As shown in FIG. 6b, when the spring clip 20 reaches the end of needle, such that the needle shaft 12 is no longer interposed between the lips 96 at the ends of the arms of the spring clip, the arms move by resilient action into the guard position blocking the needle tip 22. Retention of the spring clip 20 on the needle 12 in this position is ensured by the interlocking engaging arms 92 which prevent movement of the guard in the proximal direction and by the restraining opening 26 engaged with the needle stop 24 which prevents movement of the guard in the distal direction.

Regardless of the specific embodiment of the hypodermic needle assembly of the present invention, in each such embodiment, as the syringe plunger is advanced into the syringe, expelling the medication into the patient, the plunger extension pin 31a biases a pressure trigger longitudinally in the distal direction such that the spring clip guard 20 is automatically launched via a resilient member such as a spring along the length of a needle and over the end of the needle tip. The needle tip is therefore passively shielded by the action of pushing a syringe plunger into a syringe which has an extension pin which extends at least part way into the syringe tip. As the needle clip assembly 16 is passively actuated, the user is not required to perform any operations outside of those employed using conventional hypodermic needles. There is accordingly no need to learn any additional procedures in order to use the hypodermic needle assembly 10 according to the invention. The combined actions of the needle tip guard spring arms 92 and the needle stop 24 cause the spring clip 20 to be permanently locked in place once the injection procedure has been completed. During operation, there is only minimal frictional engagement between the spring clip 20, the needle shaft 12, and the needle hub 14. This design, ensures that the spring clip 20 will move along the needle 12 to the needle tip 22 without becoming detached therefrom or stuck thereon until the end wall 28 of the spring clip 20 engages the needle stop.

Although limited embodiments of the hypodermic needle assembly and its components have been specifically described and illustrated herein, many modifications and variations will be apparent to those skilled in the art. Accordingly, it is to be understood that the hypodermic needle assembly and its components constructed according to principles of this invention may be embodied other than as specifically described herein. The invention is defined in the following claims.

What is claimed is:

1. A safety hypodermic needle assembly comprising:
   a needle hub having open proximal and distal ends, wherein the open proximal end defines a chamber configured to engage the tip of a syringe, wherein said syringe tip has a plunger pin slidably mounted therein;
   a needle defining a longitudinal axis and having proximal and distal end portions, the distal end portion comprising a sharp needle tip and the proximal end portion being mounted in the needle hub, wherein the needle hub is configured such that the proximal end portion of the needle is in fluid communication with the syringe tip engagement chamber and the distal end portion of the needle extends out of the distal end of the needle hub;
   a needle tip safety guard assembly comprising a needle tip safety guard slidably mounted on the needle and arranged at the distal end portion of the needle hub, the needle tip safety guard assembly having a proximal end portion disposed within the open distal end of the needle hub and said needle tip safety guard having a needle opening therein through which the needle extends, the needle tip safety guard assembly being configured such that when the needle tip safety guard is urged over the needle tip, the needle tip safety guard is engaged to block the needle tip; and
   a needle guard activator assembly for urging the needle tip safety guard in a distal direction along the needle, the activator assembly comprising a pressure trigger and a resilient member, the pressure trigger being mounted in the needle hub and arranged between the syringe plunger when the syringe tip is in the syringe tip engagement chamber and the needle tip safety guard such that when the syringe plunger is translated distally, the plunger pin interacts with the pressure trigger, wherein said pressure trigger is configured to transmit the force of the plunger pin longitudinally along the axis of the needle assembly in a distal direction such that the resilient member is activated to urge the needle tip safety guard distally along the needle and over the needle tip to its blocking position.

2. A safety hypodermic needle assembly according to claim 1, wherein the needle tip safety guard is configured to prevent movement of the needle tip safety guard in a proximal direction when engaged in its needle tip blocking position.

3. A safety hypodermic needle assembly according to claim 1, wherein the needle tip safety guard comprises a spring clip having at least two opposing elongated arms resiliently biased inwardly, wherein the arms are configured to block the needle tip when the clip is engaged in its needle tip blocking position.

4. A safety hypodermic needle assembly according to claim 3, wherein the at least two opposing elongated arms further comprise inwardly projecting portions configured to engage to block the needle tip.

5. A safety hypodermic needle assembly according to claim 3, wherein the spring clip is a single integral piece.

6. A safety hypodermic needle unit according to claim 3, wherein the spring clip is made of a material having resilient memory characteristics.

7. A safety hypodermic needle assembly according to claim 3, wherein the spring dip is made of stainless steel.

8. A safety hypodermic needle assembly according to claim 1, wherein the needle tip safety guard assembly further comprises a pressure fitting in mechanical communication with the resilient member, the pressure fitting being detachably attached to the needle hub.

9. A safety hypodermic needle unit as described in claim 1, wherein the resilient member has a proximal end portion and a distal end portion, wherein the proximal end portion is fixedly attached to the pressure trigger.

10. A safety hypodermic needle unit as described in claim 1, wherein the resilient member comprises a spring.

11. A safety hypodermic needle assembly as described in claim 1, wherein the resilient member has a proximal end portion arranged within the syringe engagement chamber and the distal end portion is in mechanical communication with the proximal end of the needle tip safety guard assembly.

12. A safety hypodermic needle assembly as described in claim 1, wherein the pressure trigger is detachably attached to the needle huh at the distal end portion of the syringe tip engagement chamber and is in mechanical communication with the proximal end of the resilient member and the distal end of the plunger pin, such that when the distal end of the plunger pin mechanically interacts with the pressure trigger, the pressure trigger activates the resilient member to urge the needle tip guard distally along the needle.

13. A safety hypodermic needle assembly as described in claim 12, wherein needle guard activator assembly further comprises a pressure fitting frictionally engaged with the needle hub and in mechanical communication with the resilient member, the pressure fitting being configured such that when the distal end of the plunger pin moves the slidable pressure trigger distally, said movement is communicated through the resilient member to the pressure fitting thereby releasing the pressure fitting from its frictional engagement with the hub and allowing the resilient member to urge the needle tip guard along the needle to the needle tip.

14. A safety hypodermic needle assembly as described in claim 1, wherein the pressure trigger is removably attached to the needle hub through one of either a frictional pressure fitting or a frangible seal.

15. A safety hypodermic needle assembly as described in claim 1, wherein the needle hub further comprises a pressure trigger stop disposed within the needle hub to engage the pressure trigger such that the pressure trigger is prevented from moving distally past said stop.

16. A safety hypodermic needle assembly as described in claim 15, wherein the pressure trigger is disposed within a passageway in the needle hub and the pressure trigger stop comprises an indented section of the passageway.

17. A safety hypodermic needle assembly as described in claim 15, wherein the needle hub passageway is defined by a metal sleeve disposed within the needle hub.

18. A safety hypodermic needle assembly as described in claim 1, wherein the pressure trigger further comprises a needle hub engaging arm at its proximal end.

19. A safety hypodermic needle assembly as described in claim 1, wherein the needle huh further comprises a proximal pressure trigger stop disposed within the syringe tip engagement chamber to engage the pressure trigger to thereby prevent the pressure trigger from moving proximally past the proximal pressure trigger stop.

20. A safety hypodermic needle assembly as described in claim 19, wherein the pressure trigger further comprises at least one needle hub engaging arm at its proximal end configured to engage the proximal pressure trigger stop to thereby prevent the pressure trigger from moving proximally past the pressure trigger stop.

21. A safety hypodermic needle assembly as described in claim 19, wherein the proximal pressure trigger stop is a snap ring disposed within an annular groove formed in the syringe tip engagement chamber.

22. A safety hypodermic needle assembly as described in claim 1, wherein the pressure trigger is disposed within a passageway in the needle hub and wherein the passageway tapers such that the pressure trigger is inhibited from moving in the proximal direction.

23. A safety hypodermic needle assembly as described in claim 22, wherein the passageway comprises a metal sleeve disposed within the needle hub.

24. A safety hypodermic needle assembly as described in claim 1, wherein the needle further comprises a needle stop positioned proximate to the needle tip.

25. A safety hypodermic needle assembly as described in claim 24, wherein the needle stop comprises a crimp in the needle.

26. A safety hypodermic needle assembly as described in claim 24, wherein the needle stop comprises a sleeve on the needle.

27. A safety hypodermic needle assembly as described in claim 24, wherein the needle tip safety guard is configured such that, when the needle stop engages the needle opening in said needle tip safety guard, movement of the needle tip safety guard in the distal direction is prevented.

28. A safety hypodermic needle assembly as described in claim 1, further comprising a needle tip guard housing defining an inner volume and arranged within the open distal end of the needle hub, the needle tip guard housing being designed such that the needle tip guard is disposed therein.

29. A safety hypodermic needle assembly as described in claim 28, wherein the needle tip guard housing is detachably attached to the needle hub.

30. A safety hypodermic needle assembly as described in claim 1, wherein the syringe tip is an integral portion of the needle hub.

31. A safety hypodermic needle assembly as described in claim 1, wherein the syringe tip engagement chamber is configured to receive the tip of a syringe comprising a syringe plunger and wherein the plunger pin is an integral portion of the syringe plunger.

32. A safety hypodermic needle assembly as described in claim 31, wherein the needle hub is configured such that the syringe can be detachably attached thereto.

33. A safety hypodermic needle assembly as described in claim 31, wherein the needle hub further has engaging structure at its proximal end configured for engaging a syringe therewith.

34. A safety hypodermic needle assembly as described in claim 33, wherein the engaging structure comprises luer threads.

35. A safety hypodermic needle assembly as described in claim 1, wherein the plunger pin is of a sufficient length to extend out from the syringe tip and is configured to apply a distally directed force on the pressure trigger.

36. A safety hypodermic needle assembly as described in claim 1, further comprising an intermediate pusher assembly slidably arranged within the syringe tip engagement chamber in mechanical communication between the distal end of the plunger pin and the proximal end of the pressure trigger, the intermediate pusher assembly having an elongated arm coaxially arranged at its proximal end and configured to extend into the opening in the syringe tip and to engage the plunger pin such that the force generated by the distally eliding plunger pin is transmitted through the intermediate pusher assembly to the pressure trigger.

37. A safety hypodermic needle assembly as described in claim 1, wherein the needle is fixedly mounted within the slidable pressure trigger.

38. A safety hypodermic needle assembly as described in claim 1, wherein the needle is fixedly mounted within the needle huh such that the needle is held stationary relative to the slidable pressure trigger.

39. A safety hypodermic needle assembly as described in claim 38, wherein the needle is fixedly mounted to the needle hub by an adhesive.

40. A safety hypodermic needle assembly as described in claim 38, wherein the needle hub further comprises an opening in fluid communication with the needle, and designed to allow the adhesive to be inserted therein.

41. A safety hypodermic needle assembly as described in claim 39, wherein the pressure trigger is designed and arranged to form a fluid duct between the distal end of the syringe tip engagement chamber and the proximal end of the needle.

42. A safety hypodermic needle assembly as described in claim 39, wherein the pressure trigger is attached to the needle hub through either a frictional pressure fitting or a frangible seal.

43. A safety hypodermic needle assembly as described in claim 38, wherein the needle tip guard activator assembly comprises an elongated pressure fitting which is frictionally engaged with the needle hub and which is configured such that the needle and resilient member are disposed coaxially therein.

44. A safety hypodermic needle assembly comprising:
a needle hub having open proximal and distal ends, wherein the open proximal end defines a syringe tip engagement chamber for engaging a syringe tip of a syringe having a plunger pin slidably mounted therein;
a needle defining a longitudinal axis and having proximal and distal ends, the distal end being a sharp needle tip and the proximal end being mounted in the needle hub, wherein the needle hub is arranged such that the needle passes out of the distal end of the needle hub;
a needle tip safety guard disposed about the needle comprising:
needle tip blocking apparatus designed to block the needle tip when activated comprising an elongated resilient arm comprising a distal end wall urged radially outwardly when in a ready position by a portion of the distal end wall abutting against the needle; and a needle guard activation means such that when the plunger pin is pushed into the syringe tip engagement chamber, the needle guard activation means is longitudinally activated to activate the needle tip blocking apparatus to block the needle tip.

45. A method of inserting a needle into a patient, the method comprising:

providing a safety hypodermic needle assembly as described in claim 1;

inserting the needle into the patient to inject an injectate into said patient; and depressing the syringe plunger into the syringe until the plunger pin moves the pressure trigger a sufficient distance to thereby activate the resilient member to urge the needle tip safety guard over the needle tip such that the needle tip safety guard is engaged to block the needle tip.

46. A method of inserting a needle into a patient, the method comprising:

providing a safety hypodermic needle assembly as described in claim 44;

inserting the needle into the patient to inject an injectate into said patient; and moving the plunger pin into the syringe tip engagement chamber to thereby move the needle guard activation means a sufficient distance in a direction along the longitudinal needle axis to thereby activate the needle tip blocking apparatus to block the needle tip.

* * * * *